US008465759B2

(12) United States Patent
Crowley et al.

(10) Patent No.: US 8,465,759 B2
(45) Date of Patent: Jun. 18, 2013

(54) PROCESS FOR THE PREPARATION OF A HOT-MELT EXTRUDED LAMINATE

(75) Inventors: Michael M. Crowley, Austin, TX (US); Justin M. Keen, Austin, TX (US); John J. Koleng, Austin, TX (US); Feng Zhang, Austin, TX (US)

(73) Assignee: Auxilium US Holdings, LLC, Wilmington, DE (US)

( * ) Notice: Subject to any disclaimer, the term of this patent is extended or adjusted under 35 U.S.C. 154(b) by 597 days.

(21) Appl. No.: 12/294,372

(22) PCT Filed: Mar. 22, 2007

(86) PCT No.: PCT/US2007/064713
§ 371 (c)(1),
(2), (4) Date: Sep. 24, 2008

(87) PCT Pub. No.: WO2007/112285
PCT Pub. Date: Oct. 4, 2007

(65) Prior Publication Data
US 2009/0136555 A1 May 28, 2009

Related U.S. Application Data

(60) Provisional application No. 60/785,590, filed on Mar. 24, 2006.

(51) Int. Cl.
A61F 13/00 (2006.01)
A61K 47/00 (2006.01)
A61L 15/00 (2006.01)
B29C 47/06 (2006.01)
B32B 37/00 (2006.01)

(52) U.S. Cl.
USPC ........ 424/424; 264/148; 264/153; 264/173.1; 264/173.12; 264/173.15; 264/173.16; 264/211; 424/425; 424/426; 424/427; 424/428; 424/430; 424/434; 424/435; 424/436; 424/437; 424/439; 424/443; 424/445; 424/447; 424/448; 424/449; 514/953; 514/954; 514/956

(58) Field of Classification Search
None
See application file for complete search history.

(56) References Cited

U.S. PATENT DOCUMENTS

| 3,017,304 | A | | 5/1956 | Burgeni |
| RE33,093 | E | | 10/1989 | Schiraldi et al. |
| 5,095,619 | A | * | 3/1992 | Davis et al. ........................ 30/41 |
| 5,318,737 | A | * | 6/1994 | Trabert et al. ............ 264/173.16 |
| 5,614,223 | A | * | 3/1997 | Sipos ............................. 424/489 |
| 5,662,926 | A | | 9/1997 | Wick et al. |
| 5,676,969 | A | | 10/1997 | Wick et al. |

(Continued)

FOREIGN PATENT DOCUMENTS

| EP | 0250187 A2 | 12/1987 |
| EP | 1 493 561 A2 | 1/2005 |

(Continued)

OTHER PUBLICATIONS

Zhang et al., "Properties of Sustained-Release Tablets Prepared by Hot-Melt Extrusion," Pharmaceutical Development and Technology, 4(2), 241-250 (1999).

(Continued)

Primary Examiner — Jeffrey Wollschlager
(74) Attorney, Agent, or Firm — RatnerPrestia

(57) ABSTRACT

A process for the preparation of a bioadhesive laminate comprising a hot-melt extruded reservoir layer and a hot-melt extruded backing layer is provided. The reservoir layer comprises a thermoplastic bioadhesive composition containing an active agent. An active agent-containing thermoplastic bioadhesive hydrophilic composition is hot-melt coextruded with a hydrophobic composition to form at least a bi-layered laminate. The hydrophilic composition and the hydrophobic composition have at least one polymer in common. In addition, the melt flow index of the hydrophobic composition is within 50% of the melt flow index of the hydrophilic composition. As a result, the laminate has a uniform transverse cross-section and/or a uniform longitudinal cross-section throughout a major of the length of the laminate. Moreover, when the laminate is divided into unit doses of approximately the same size, they have a high degree of content uniformity with respect to the active agent(s) present therein.

16 Claims, 12 Drawing Sheets

U.S. PATENT DOCUMENTS

| | | | |
|---|---|---|---|
| 5,679,373 A | | 10/1997 | Wick et al. |
| 5,700,478 A | | 12/1997 | Biegajski et al. |
| 5,766,620 A | * | 6/1998 | Heiber et al. .............. 424/436 |
| 5,851,551 A | | 12/1998 | Tseng et al. |
| 5,939,099 A | | 8/1999 | Grabowski et al. |
| 5,998,431 A | * | 12/1999 | Tseng et al. .............. 514/300 |
| 6,010,715 A | | 1/2000 | Wick et al. |
| 6,048,547 A | | 4/2000 | Seth et al. |
| 6,071,539 A | | 6/2000 | Robinson et al. |
| 6,072,100 A | | 6/2000 | Mooney et al. |
| 6,375,963 B1 | | 4/2002 | Repka et al. |
| 6,528,089 B1 | | 3/2003 | Kothrade et al. |
| 6,555,131 B1 | | 4/2003 | Wolff et al. |
| 6,562,369 B2 | | 5/2003 | Luo et al. |
| 6,585,997 B2 | * | 7/2003 | Moro et al. ............... 424/434 |
| 6,649,186 B1 | | 11/2003 | Robinson et al. |
| 6,753,370 B2 | | 6/2004 | Nakatsukasa et al. |
| 2003/0110630 A1 | | 6/2003 | Onishi et al. |
| 2003/0141625 A1 | * | 7/2003 | Shelby et al. ........... 264/173.11 |
| 2005/0058602 A1 | * | 3/2005 | Ramji et al. .................. 424/9.6 |
| 2005/0100515 A1 | * | 5/2005 | Sagel et al. .................. 424/53 |
| 2005/0281757 A1 | * | 12/2005 | Ibrahim et al. ............... 424/49 |

FOREIGN PATENT DOCUMENTS

| | | | |
|---|---|---|---|
| EP | 1 493 561 A3 | 1/2005 | |
| JP | 63019152 A | 11/1994 | |
| JP | 2001508037 A | 6/2001 | |
| JP | 2002248124 A | 9/2002 | |
| JP | 2004521085 A | 7/2004 | |
| WO | WO-9817251 A1 | 4/1998 | |
| WO | WO-99/13812 A1 | 3/1999 | |
| WO | WO-00/19975 A1 | 4/2000 | |
| WO | WO-00/24382 A2 | 5/2000 | |
| WO | WO-00/24382 A3 | 5/2000 | |
| WO | WO-0241878 A2 | 5/2002 | |
| WO | WO 03/101357 | 12/2003 | |

OTHER PUBLICATIONS

Zhang et al., "Properties of Hot-Melt Extruded Theophylline Tablets Containing Poly(Vinyl Acetate)," *Drug Development and Industrial Pharmacy*, 26(9), 931-942 (2000).

De Brabander et al., "Development and evaluation of sustained release mini-matrices prepared via hot melt extrusion," *Journal of Controlled Release*, 89 (2003) 235-247.

De Brabander et al., "Bioavailability of ibuprofen from hot-melt extruded mini-matrices," *International Journal of Pharmaceutics* 271 (2004) 77-84.

Huang et al., "Effects of Operational Parameters on the Performance of a Heat-Melt Extruder," *The Chinese Pharmaceutical Journal*, 2003, 55, 463-472.

Repka et al, "Influence of Vitamin E TPGS on the properties of hydrophilic films produced by hot-melt extrusion," *International Journal of Pharmaceutics*, 202 (2000) 63-70.

Crowley, "Physicochemical and Mechanical Characterization of Hot-Melt Extruded Dosage Forms," Dissertation—Presented to the Faculty of the Graduate School of The University of Texas at Austin, May 2003.

Crowley et al, "Stability of polyethylene oxide in matrix tablets prepared by hot-melt extrusion," *Biomaterials*, 23 (2002) 4241-4248.

Aitken-Nichol et al., "Hot Melt Extrusion of Acrylic Films," *Pharmaceutical Research*, vol. 13, No. 5, 1996, pp. 804-808.

McGinty et al., "Hot-Melt Extruded Films for Transmucosal & Transdermal Drug Delivery Applications," *Drug Delivery Technology*, Sep. 2004, vol. 4, No. 7, pp. 40-47.

Blatz et al., "Interlaminar Adhesives for Coextruding," *Paper, Film & Foil Converter*, Jan. 1979, pp. 102 and 104.

Apicella et al., "Poly(ethylene oxide) (PEO) and different molecular weight PEO blends monolithic devices for drug release," *Biomaterials*, 1993, vol. 14, No. 2, pp. 83-90.

Manish, Munjal, et al.; "Chemical Stabilization of A Δ9 Tetrahydrocannabinol Prodrug in Polymeric Matrix Systems Produced by a Hot-Melt Method: Role of Microenvironment pH"; AAPS Pharmscitech; vol. 7, No. 3, Sep. 1, 2006.

Repka, M A, et al; "Characterization of Cellulosic Hot-Melt Extruded Films Containing Lidocaine"; European Journal of Pharmaceutics and Biopharmaceutics, Elsevier Science Publishers B.V., Amsterdam, NL., vol. 59, No. 1, pp. 189-196, available online Sep. 1, 2004.

\* cited by examiner

Drug Release of 11.0% Testosterone Transmucosal Film in 0.1% SLS in SSF pH 6.75

Drug Release of 11.0% Testosterone Transmucosal Film in 0.1% SLS in SSF pH 6.75

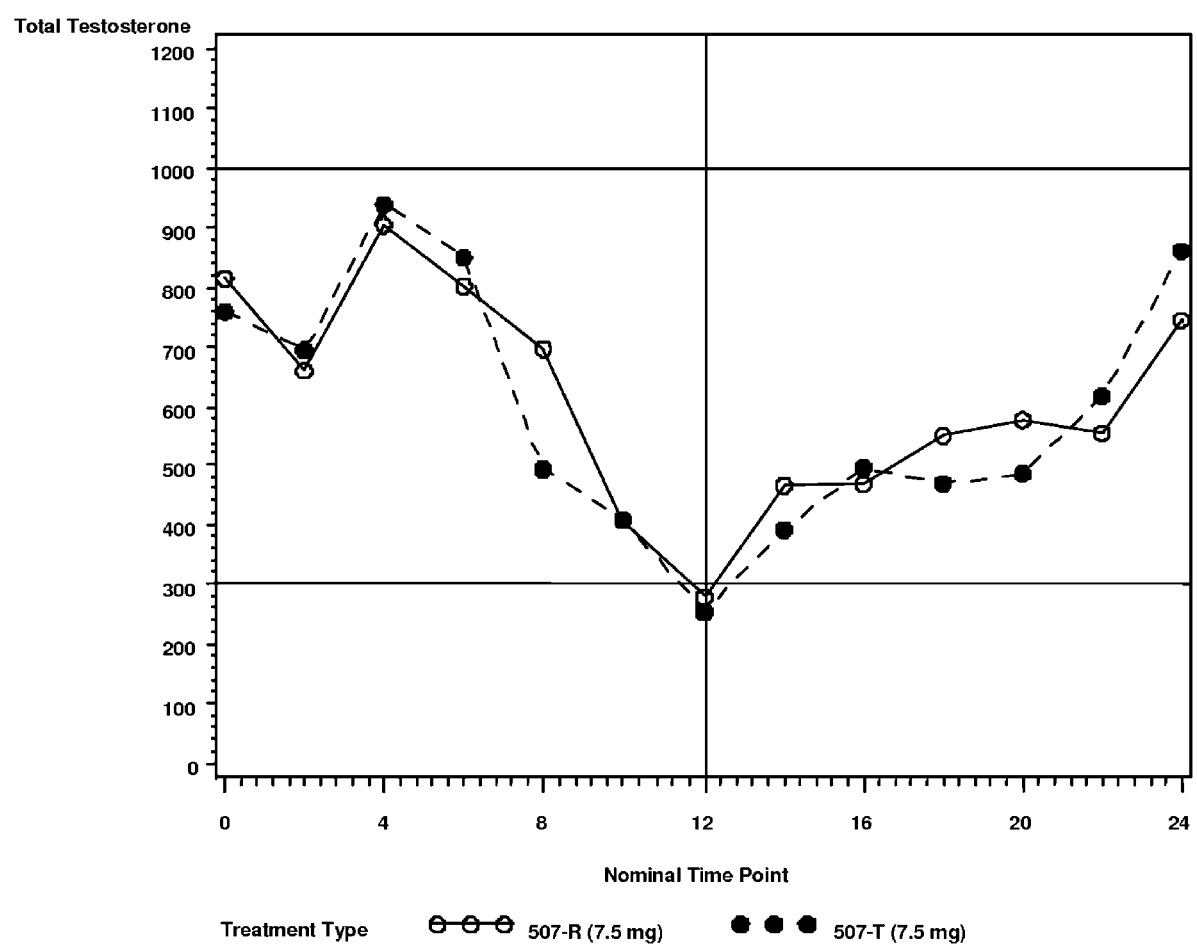

PROCESS FOR THE PREPARATION OF A HOT-MELT EXTRUDED LAMINATE

This application is the U.S. National Phase Application of PCT International Application No. PCT/US2007/064713, filed Mar. 22, 2007 (incorporated by reference herein in its entirety), and claims priority of U.S. Provisional Patent Application No. 60/785,590, filed Mar. 24, 2006.

FIELD OF THE INVENTION

The present invention concerns a process for the preparation of a hot-melt extruded (HME) laminate. In particular, the invention concerns a multi-layered laminate comprising at least two hot-melt extruded layers that are coextruded to form the laminate.

BACKGROUND OF THE INVENTION

A number of patents disclose transdermal or buccal dosage forms containing testosterone and include cast and extruded films, including U.S. Pat. No. 6,585,997 (U.S. Pregrant Patent Application Publication No. 20030044446) to Moro et al. (Access Pharmaceuticals); U.S. Pat. No. 6,562,369 to Luo et al. (Dermatrends Inc.); U.S. Pat. No. 6,555,131 to Wolff et al. (Schwarz Pharma AG); U.S. Pat. No. 6,010,715, U.S. Pat. No. 5,679,373, U.S. Pat. No. 5,662,926, and U.S. Pat. No. 5,676,969 to Wick et al. (Bertek Inc.); and PCT International Patent Application Publication No. WO 00/19975.

Many researchers have utilized hot-melt extrusion techniques to produce pharmaceutical preparations in various forms, including films. Aitken-Nichol et al. (Aitken-Nichol, C., F. Zhang, and J. W. McGinity, *Hot Melt Extrusion of Acrylic Films*. Pharmaceutical Research, 1996. 13(5): p. 804-808) used hot-melt extrusion methods to produce acrylic polymer films containing the active lidocaine HCl. Grabowski et al. (Grabowski, S., et al., *Solid active extrusion compound preparations containing low-substituted hydroxypropylcellulose*. 1999: U.S. Pat. No. 5,939,099 WO9625151 DE19504832 EP0809488) produced solid pharmaceutical preparations of actives in low-substituted hydroxypropyl cellulose using hot-melt extrusion techniques. Repka and McGinity (Repka, M. A. and J. W. McGinity, *Hot-melt extruded films for transmucosal & transdermal drug delivery applications*. Drug Delivery Technology, 2004. 4(7): p. 40, 42, 44-47) used hot-melt extrusion processes to produce bioadhesive films for topical and mucosal adhesion applications for controlled drug delivery to various mucosal sites (Repka, M. A., S. L. Repka, and J. W. McGinity, *Bioadhesive hot-melt extruded film for topical and mucosal adhesion applications and drug delivery and process for preparation thereof*. Apr. 23, 2002: U.S. Pat. No. 6,375,963).

Lamination of solidified or semi-solidified extruded films is known in the polymer processing industry. Lamination is generally considered a two-step process wherein two extrudates are first prepared individually, albeit simultaneously or sequentially, thereby forming solidified or semi-solidified (softened but no molten) extrudates. The extrudates are then laminated using a conventional lamination process. Such processes typically require the use of an adhesive between the solid or semi-solid layers followed by pressing them together and/or the application of heat and pressure to the layers by passing them simultaneously through heated rollers (For example, see U.S. Pat. No. 5,700,478, U.S. Pat. No. 5,851,551, U.S. Pat. No. 5,998,431). The lamination process can be done immediately after extrusion or some period of time afterwards.

Coextrusion is a process whereby two or more material feed streams, at least one of which is molten, are brought together and placed in contact with one another prior to exiting through an extrusion die. In one process, both material feed streams are molten prior when they are placed in contact with one another. In an alternate process, one material feed stream is molten and the second material feed stream is a preformed solid or semi-solid extrudate onto which the first material is placed prior to extrusion through a die. Coextrusion can be achieved using different types of dies: a dual manifold (or multi-manifold) die or a feed block die assembly, each of which is described below.

European Patent Application EP 1493561 (U.S. Pat. No. 6,638,637) discloses the preparation of a bilayered film by coextrusion of a primary layer containing propylene copolymer with a secondary layer containing propylene copolymer or homopolymer. The melting point of the two layers is different.

U.S. Pat. No. 6,753,370 (Japanese patent application no. JP 09327851) discloses the preparation of a bilayered film by coextrusion of a polyamide (PA) resin with a saponified ethylene-vinyl acetate (EVOH) copolymer such that the melt viscosity of the PA resin is greater than that of the EVOH copolymer.

U.S. Pregrant patent application publication no. 2003000501 discloses a method of preparing a multi-layered adhesive film wherein an adhesive composition containing an amine-modified, low acid ethylene-methacrylic acid copolymer having a specified melt index is coextruded with an aliphatic polyketone copolymer.

Blatz (*PAP. FILM FOIL CONVERTER*, vol 53 no 1 Jan. 1979 pp 102-104) discloses a method of employing interlaminar adhesives for lamination of films in order to prepare multi-layered films.

U.S. Pat. No. 6,010,715, U.S. Pat. No. 5,679,373, U.S. Pat. No. 5,662,926, and U.S. Pat. No. 5,676,969 to Wick et al. (Bertek Inc.) discloses a transdermal patch "for the controlled release of an active agent to the skin or mucosa of a host. The patches are laminates of a backing layer and a monolithic carrier layer formed from a melt blend of an active ingredient with a thermoplastic matrix polymer.

U.S. Pat. No. 6,375,963 to Repka et al. discloses a bioadhesive hot-melt extruded mono-layered or multi-layered film composition comprising a water swellable or water soluble thermoplastic polymer and a bioadhesive polymer optionally containing an organic acid, a superdisintegrant, a super-absorbent and/or an antioxidant.

U.S. Pat. No. RE 33,093 to Schiraldi et al. describes a bioadhesive hot-melt extruded film for intra-oral drug delivery and the processing thereof. The film comprises essentially a bioadhesive layer consisting of 40-95% by weight of a hydroxypropylcellulose (HPC), 5-60% of a homopolymer of ethylene oxide (PEO), 0-10% of a water-insoluble polymer, a medicament and 2-10% of a plasticizer. The film is made by a hot-melt extrusion process. A multi-layered film can be made.

U.S. Pat. No. 6,072,100 to Mooney et al. discloses an extruded composition containing "a thermoplastic water-soluble polymer selected from the group consisting of hydroxypropyl cellulose and polyethylene oxide; a water-soluble polymer derived from acrylic acid; medicament; and plasticizer." They disclose a mono-layered or multi-layered composition.

PCT International Patent Publication No WO 99/13812 to Moo-Young et al. (The Population Council) discloses a melt-extruded transdermal formulation for the delivery of an androgen via the skin or mouth.

However, prior art processes for the preparation of heat laminated multi-layered laminates via hot-melt coextrusion often result in the formation of non-uniform laminates. Such films have a non-uniform transverse cross-section, meaning that the transverse cross-section of the laminate varies along the longitudinal axis of the laminate as it is produced by coextrusion. Non-uniformity is highly undesirable in the pharmaceutical industry as it leads to variable dosage strength from one unit dose to another.

None of these references describe a hot-melt coextruded laminate, and process therefor, possessing the advantageous properties as described herein.

SUMMARY OF THE INVENTION

The invention provides a process for preparing a bi-layered hot-melt co-extruded laminate having a uniform transverse cross-section throughout a major portion of the length of the laminate. The invention also provides products of the process. The process requires coextrusion wherein the layers adhere to one another without requiring an adhesive between the layers. The first layer is a hydrophilic bioadhesive drug reservoir hot-melt extruded layer comprising a thermoplastic, water soluble, swellable or erodible polymer, a bioadhesive polymer, testosterone, a lubricant/antioxidant and optionally one or more other excipients. The second layer is a hydrophobic non-bioadhesive low-permeability hot-melt extruded backing layer that optionally excludes an active agent. The process comprises:

a) providing a thermoplastic hydrophilic first composition comprising at least one bioadhesive polymer, at least one water swellable or water soluble thermoplastic polymer, an active agent, an antioxidant (and/or lubricant), and optionally one or more hydrophobic polymers, one or more other excipients or a combination thereof;

b) providing a thermoplastic hydrophobic second composition comprising at least one hydrophobic polymer, a plasticizer, optionally one or more hydrophilic polymers, one or more other excipients, or a combination thereof;

c) coextruding the first composition and the second composition to form a bioadhesive hydrophilic reservoir layer and a hydrophobic low permeability backing layer, respectively; wherein the first and second compositions comprise at least one polymer in common.

By "comprise at least one polymer in common" is meant the first composition and the second composition comprise a same hydrophilic polymer and/or a same hydrophobic polymer. It is not necessary for the at least one polymer in common to have the exact combination of physical properties in each occurrence. It is only necessary that the at least one polymer in common have substantially the same or substantially the same chemical formula in each occurrence, even though the polymer can have different average molecular weights in each occurrence, or at least that the reservoir composition and backing composition be sufficiently miscible to permit good inter-laminar adhesion via hot-melt extrusion, heat catalyzed lamination. For example, if PEO is the at least one polymer in common, the PEO in the reservoir layer can have a different average molecular weight (or solution viscosity) than the PEO in the backing layer. In other words, PEO can be present in different grades in the two layers but it would still be considered as at least the one polymer in common. In a similar fashion, PEO and poly(ethylene glycol) (PEG) have a very similar chemical structure as they are both derived from the same monomer (ethylene oxide). In such a case, PEO and PEG would be considered a polymer in common.

If the first composition comprises a hydrophobic polymer, it is present in a low enough amount that the reservoir layer retains its in-use bioadhesive and hydrophilic nature. Likewise, if the second composition comprises a hydrophilic polymer, it is present in a low enough amount that the backing layer retains its in-use non-bioadhesive and hydrophobic nature. The invention provides embodiments wherein the first and second composition comprise one, two, three or more polymers in common.

The laminate has a high degree of content uniformity when divided into unit doses. In some embodiments, the laminate has a uniform transverse cross-section throughout a major portion of its length. In some embodiments, the laminate has a uniform longitudinal cross-section throughout a major portion of its length.

In some embodiments, each of the layers is pliable enough to facilitate manual placement on and manual conformance to the mucosa of a subject to which the laminate is applied.

Some embodiments of the process require that the layers possess approximately the same melt flow index (melt flow rate, melt flow), meaning that their melt flow indices will fall within individual predefined ranges and that those ranges overlap at least to some predefined extent. For example, if the melt flow index of the reservoir layer is within range X and the melt flow index of the backing layer is within range Y, then range X overlaps with or is the same as range Y. The invention provides embodiments wherein the melt flow index of the first composition is from 0.1 to 60,000 and the melt flow index of the second composition is from 0.8 to 40. The invention also includes embodiments, wherein the melt flow index of the first composition is within 50% of the melt flow index of the second composition or vice versa. In some embodiments, the melt flow index of the first composition is within 200%, 100% 50% or 10% of the melt flow index of the second composition. In terms of the ratio of melt flow index of one composition to the other, the ratio can vary from 10:1 to 1:10, 5:1 to 1:5, or 2:1 to 1:2. The melt viscosity ranges defined herein were determined according to the method(s) cited or described herein. Melt flow index is measured using ASTM Method D1238. Comparison of melt flow index values can only be accomplished if both values were obtained using the same instrumental parameters. Melt flow index values will vary depending on the sample load, the weight used, the diameter of the orifice and temperature.

According to some embodiments, the first composition comprises two or more thermoplastic and water swellable, water soluble or water erodible polymers; and/or the second composition comprises two or more different hydrophobic polymers.

The second composition optionally includes an active agent; so that some embodiments exclude an active agent and other embodiments include one or more active agents.

The laminate is used to treat one or more disorders therapeutically responsive to the active agent(s) included within the laminate. For example, if the laminate comprises testosterone, then it can be used to treat one or more disorders associated with testosterone deficiency, e.g. hypogonadism, Peyronie's disease, priapism, impotence, erectile dysfunction, reduced libido, loss of muscle mass, etc.

During use, the bioadhesive layer absorbs water, such as applied water or water from saliva or other bodily fluids, and is applied transdermally to a subject whereby the laminate begins to release active agent in a controlled manner. In one embodiment, the method of use requires the buccal administration of a bi-layered device containing testosterone in controlled release form.

Another aspect of the invention provides a process for the preparation of a bioadhesive hot-melt coextruded bi-layered laminate comprising:

a) providing a thermoplastic hydrophilic first composition comprising at least one bioadhesive polymer, at least one water swellable or water soluble thermoplastic polymer, testosterone, an antioxidant (and/or lubricant), and optionally one or more hydrophobic polymers, one or more other excipients, or a combination thereof;

b) providing a thermoplastic hydrophobic second composition comprising at least one hydrophobic polymer, a plasticizer, and optionally one or more hydrophilic polymers, one or more other excipients, or a combination thereof;

c) coextruding the first composition and the second composition to form a laminate comprising a bioadhesive hydrophilic reservoir layer and a hydrophobic low permeability backing layer, respectively; wherein d) the reservoir layer and the backing layer comprise at least one polymer in common; and e) the melt flow index of the first composition is within 50% of the melt flow index of the second composition.

The inventors have discovered that a drug reservoir layer that comprises at least two different thermoplastic polymers can result in substantially improved release profiles. In general, the backing layer can comprise about 10 to about 60% wt. of the laminate, and/or the reservoir layer can comprise about 40 to about 90% wt. of the laminate.

The pharmaceutical composition is formulated such that drug therein may or may not be dissolved during extrusion. In some embodiments, the active agent has been solubilized in the reservoir layer during hot-melt extrusion thereof.

Any fine particle of drug made by any fine particle production technology can be incorporated into the claimed pharmaceutical composition. Drug-containing particles are dispersed within the matrix via melt processing.

The multi-layered laminate (or the unit dose derived therefrom) can be in the shape of a sheet, rod, tablet, pill, capsule, tube, strand, geometric form, non-geometric form or cylinder. A laminate will comprise at least two layers: a bioadhesive drug reservoir layer and a backing layer. In one embodiment, the backing layer of the laminate also includes an acidic component, so as to minimize any interfacial degradation that might occur at the interface of the reservoir layer and the backing layer.

The invention also provides a process for the manufacture of plural unit doses of a bioadhesive multi-layered laminate adapted for transdermal delivery of one or more active agents.

Lamination of the individual layers can be conducted by simultaneously passing the heated layers between opposing rollers that force the layers together. The heat catalyzed lamination step is conducted after the layers have been monolayer extruded and are heated or still hot from the extrusion step. Accordingly, bi-layered laminate can be made according to a process comprising:

providing an inert composition comprising a hydrophobic polymer;

providing an active agent-containing composition comprising active agent dispersed within a thermoplastic bioadhesive composition;

hot-melt extruding the inert composition to form a solid or semi-solid backing layer;

hot-melt extruding the active agent-containing composition to form an solid or semi-solid active agent reservoir layer; and laminating the backing layer and active agent reservoir layer together thereby forming the multi-layered laminate; wherein the inert composition and the active agent-containing composition comprise at least two polymers in common; the melt flow index of the inert composition is within 50% of the melt flow index of the active-agent containing composition; the laminate has a uniform transverse cross-section along a major portion of its length; and the unit doses have a content uniformity of 85%-115% of label claim, 90%-110% of label claim, or 95%-105% of label claim. In some embodiments, the actual content of drug in individual unit doses prepared from the same batch of laminate will vary by no more than ±15%, ±10%, ±5%, or ±2% of the average content of drug determined for the entire lot of unit doses obtained from the same laminate.

Following lamination or coextrusion, the laminate can be divided into plural unit doses having a high content uniformity for the active agent.

For the lamination process, each film can be extruded individually or separately from the other film at the same or different times. In other words, the films can be extruded simultaneously or sequentially and subsequently laminated in solidified or semi-solidified form.

Some embodiments of the invention include those wherein the process further comprises applying a release liner layer to the laminate before of after dividing the laminate into plural unit doses.

The invention can include combinations of two or more embodiments disclosed herein.

BRIEF DESCRIPTION OF THE FIGURES

The following figures form part of the present description and describe exemplary embodiments of the claimed invention. The skilled artisan will be able, in light of these figures and the description herein, to practice the invention without undue experimentation.

FIG. 3a depicts a top plan view of the laminate of FIG. 1a.

FIG. 14a depicts the testosterone mean plasma concentration after several days of dosing (day 3 of 13) for human subjects to which an extended release dosage form of the invention has been administered.

DETAILED DESCRIPTION OF THE INVENTION

Figure 1A:
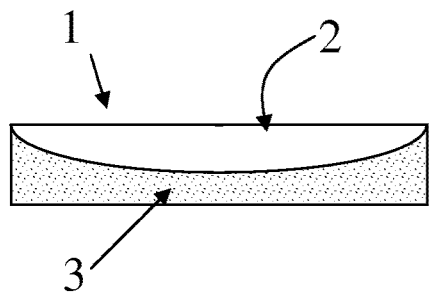
FIGS. 1a-1e depict transverse cross-sectional elevations of exemplary embodiments of hot-melt coextruded laminates having a non-uniform transverse cross-section throughout a major portion of its length prior to being divided into unit doses.

The invention provides a coextruded multi-layered laminate comprising a HME active agent-containing reservoir layer and a hot-melt extruded backing layer. The reservoir layer can be a controlled release thermoplastic bioadhesive matrix. The backing layer is an optionally-inert backing layer. By "optionally-inert backing layer" is meant that the backing layer is optionally inert. Therefore, the backing layer can be inert and exclude active agent or it can be therapeutic and include active agent.

A unit dose of the laminate provides a therapeutically effective amount of active agent following transdermal administration to a subject. As used herein, the term "transdermal administration" is taken to mean application of the laminate to a dermal or mucosal surface of the body in a subject, whereby the bioadhesive nature of the laminate, in particular the reservoir layer, causes it to removably adhere to the surface. Accordingly, transdermal encompasses the term transmucosal. As used herein, the term "transmucosal administration" is taken to mean application of the laminate to a mucosal surface of the body in a subject, whereby the bioadhesive nature of the laminate, in particular the reservoir layer, causes it to removably adhere to the surface. Dermal and mucosal modes of administration include skin, buccal, sublingual, subdermal, urethral, rectal, nasal, vaginal, ophthalmic, or otic administration, or as an implantable drug delivery device.

The term "hot-melt extrusion" or "hot-melt extruded" is used herein to describe a process whereby a blended composition is heated and/or compressed to a molten (or softened) state and subsequently forced through an orifice where the extruded product (extrudate) is formed into its final shape in which it solidifies upon cooling. The blended composition is conveyed through one or more heating zones typically by a screw mechanism. The screw or screws are rotated by a variable speed motor inside a cylindrical barrel where only a small gap exists between the outside diameter of the screw and the inside diameter of the barrel. In this conformation, high shear is created at the barrel wall and between the screw fights by which the various components of the powder blend are well mixed and disaggregated. As used herein, the term "extrudate" refers to a HME composition. The term "coextrusion" is taken to mean an extrusion process in which at least two different melt compositions are extruded substantially simultaneously through a dual confining orifice to form respective first and second layers of a laminate, whereby the sum total cross-sectional area of the two layers corresponds substantially to the cross-sectional area of the exit orifice in the extrusion die. The term "lamination" is taken to mean an extrusion process in which at least two different layers are hot-melt extruded and combined after exiting the extrusion orifice and then bonded by a set of opposing rollers. The lamination can be conducted with heat, pressure, adhesive and/or solvent.

The term "hot-melt extrudable" refers to a material or composition that can be hot-melt-extruded with no significant thermal degradation, e.g. less than 5% wt. or less than 10% wt. degradation. The term "thermally processable" is taken to mean a material or composition that softens or melts at the extrusion processing temperature with no significant thermal degradation.

Figure 3A:
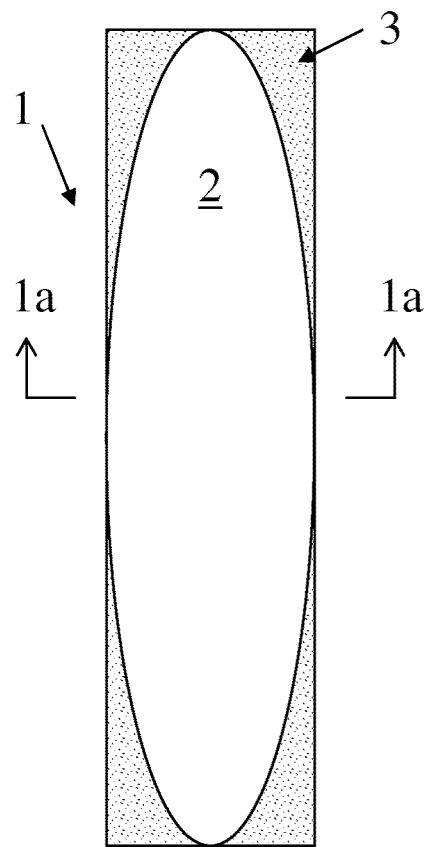

FIG. 1a depicts a conceptual transverse cross-sectional elevation of a bi-layered hot-melt extruded laminate (1) comprising a drug reservoir (3) and a backing layer (2). After coextrusion and or lamination but before being divided into unit doses, the laminate has a non-uniform transverse cross-section throughout a major portion of its length. The term "non-uniform transverse cross-section" refers to a laminate in which the transverse cross-section of a first portion of the laminate changes substantially from the transverse cross-section of a second portion of the laminate. For example, the transverse cross-sectional shape of the one or more of the layers of the laminate changes when comparing two different spaced apart linear portions of the laminate. FIG. 3a depicts a top plan view of the laminate (1). The shape of the backing layer (2) changes when viewed along the linear axis (or length) of the laminate resulting in a substantial change of the transverse cross-section of the film along different portions of its length.

The non-uniform laminate (1) is the product of a HME process wherein the melt flow index of each of the two layers is not within a necessary range. In this particular example, the melt flow index of the reservoir layer is unsuitably higher than the melt flow index of the backing layer. This type of non-uniform laminate can be prepared with a feed block type die assembly.

Figure 1B:
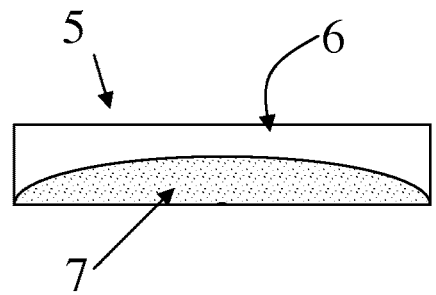
Figure 1C:
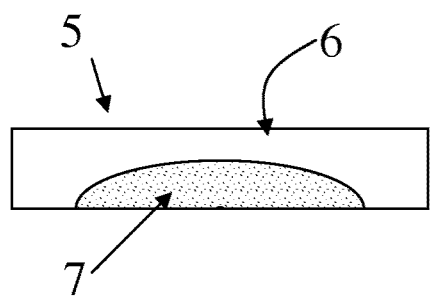
Figure 3B:
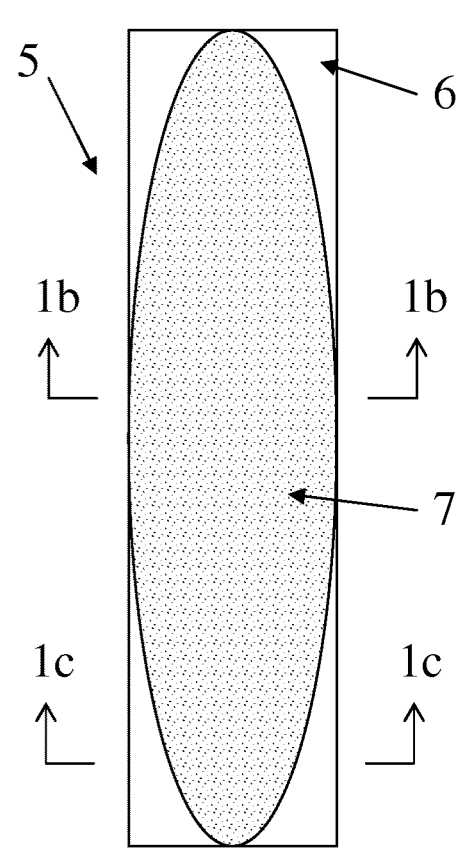
FIG. 3b depicts a top plan view of the laminate of FIGS. 1b and 1c.

FIGS. 1b-1c depict two different conceptual transverse cross-sectional elevations of a bi-layered hot-melt extruded laminate (5) having a non-uniform transverse cross-section along its length and comprising a drug reservoir (7) and a backing layer (6). FIG. 3b depicts a bottom plan view of the laminate (5). The transverse cross-section depicted in FIG. 1b is substantially different than the transverse cross-section depicted in FIG. 1c. This is because the shape of the drug reservoir layer changes substantially as determined along linear axis of the laminate. In this particular example, the melt flow index of the reservoir layer is unsuitably lower than the melt flow index of the backing layer.

Figure 1D:
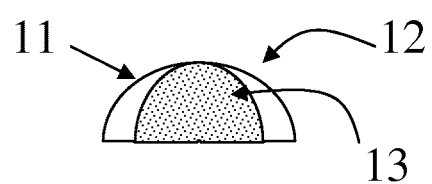

FIG. 1d depicts a transverse cross-section of a hemi-cylindrical laminate (11) comprising a backing layer (12) and a drug-reservoir layer (13). The backing layer has a non-uniform transverse cross-section as determined along the length of the laminate.

Figure 1E:
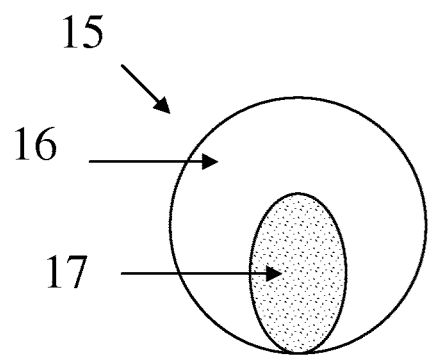

FIG. 1e depicts a transverse cross-sectional elevation of a bi-layered rod-shaped laminate (15) comprising a backing layer 16 and a reservoir layer (17). The laminate has a non-uniform transverse cross-section along its linear axis as determined by comparing the transverse cross-section of the laminate at two or more different points along its length.

Figure 2A:
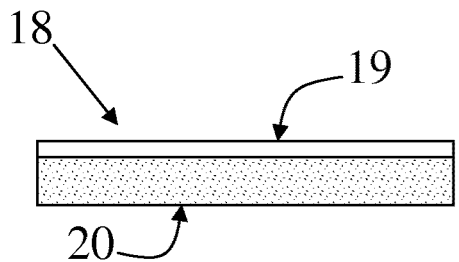
FIGS. 2a-2e depict transverse cross-sectional elevations of exemplary embodiments of hot-melt coextruded laminates having a uniform transverse cross-section throughout a major portion of their length prior to being divided into unit doses.

FIG. 2a depicts a transverse cross-section of a bi-layered laminate (18) comprising a backing layer (19) and a reservoir layer (20). This laminate has a uniform transverse cross-section because it does not change substantially throughout a major portion of the length of the laminate. Uniformity was determined by comparing the transverse cross-section of a first length of the laminate with the transverse cross-section of a spaced apart second length of the laminate. The backing layer (19) comprises a minor portion of the laminate (18) and the reservoir layer (20) comprises a major portion of the laminate.

Figure 2B:
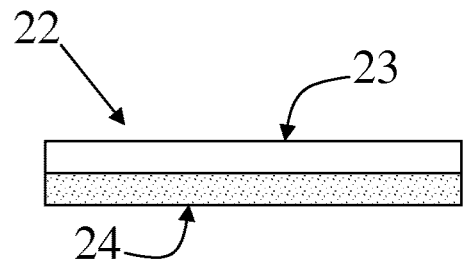

FIG. 2b also depicts a transverse cross-section of a laminate (22) having a uniform transverse cross-section. The laminate comprises a backing layer (23) and a reservoir layer (24), each of which comprises an approximately equal portion of the laminate.

Figure 2C:
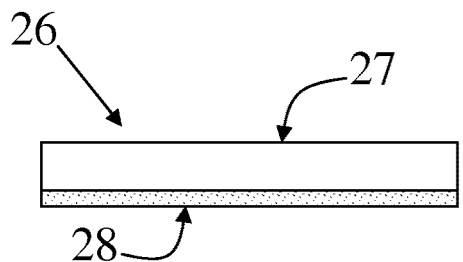

FIG. 2c depicts a transverse cross-section of a laminate (26) having a uniform transverse cross-section. The laminate comprises a backing layer (27) and a reservoir layer (28). The backing layer comprises a major portion of the laminate, and the reservoir layer comprises a minor portion of the laminate.

Figure 2D:
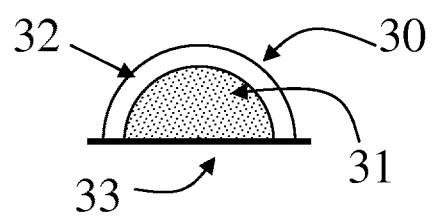

FIG. 2d depicts a transverse cross-section of a hemi-cylindrical laminate (30) comprising a backing layer (32), a release liner layer (33) and a drug-reservoir layer (31). The laminate has a uniform transverse cross-section as determined along the length of the laminate. The release liner layer can be added to the laminate after coextrusion of the laminate. Otherwise, it can be coextruded with the reservoir and backing layers of the laminate.

Figure 2E:
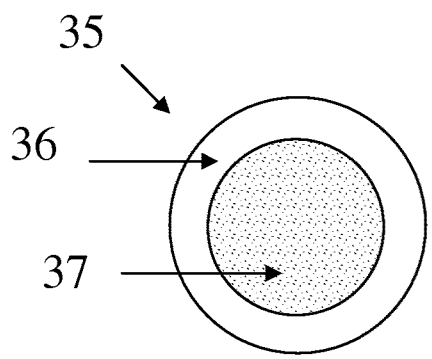

FIG. 2e depicts a transverse cross-section of a bi-layered rod-shaped laminate (35) comprising a backing layer (36) and a reservoir layer (37). This laminate has a uniform transverse cross-section as determined by comparing two or more transverse cross-sections of spaced apart portions along the length of the laminate.

Figure 3C:
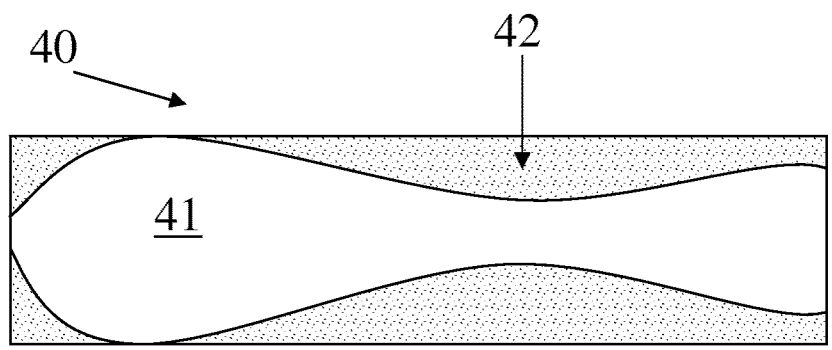
FIG. 3c depicts a top plan view of another laminate having a non-uniform transverse cross-section.

FIG. 3c depicts a top plan view of a laminate (40) comprising a backing layer (41) and a reservoir layer (42). The laminate has a non-uniform transverse cross-section along its length since the width and/or depth of the backing layer changes along the length of the laminate.

Figure 4A:
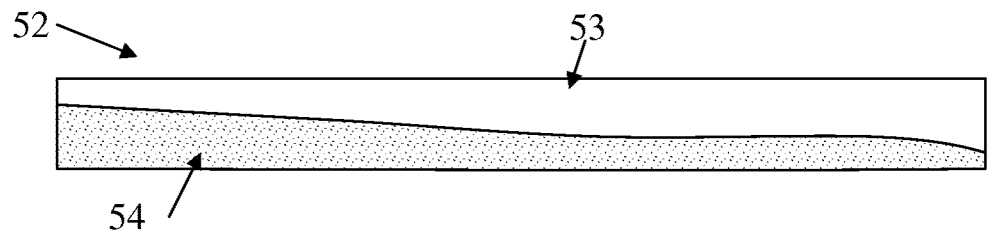
FIGS. 4a-4b depict longitudinal cross-sectional elevations along the linear axis of laminates having a non-uniform longitudinal cross-section across the transverse width of the laminate.

Depending upon the process used, a laminate may have a uniform or non-uniform longitudinal cross-section. FIG. 4a depicts a laminate (52) having a non-uniform longitudinal cross-section. The shape of the longitudinal cross-section of the backing layer (53) and the reservoir layer (54) changes along the linear axis (or length) of the laminate. Uniformity or non-uniformity of the longitudinal cross-section is determined by comparing the longitudinal cross-section of a laminate along different portions of its transverse width. For example, the longitudinal cross-section of the left-most portion of a laminate can be compared to the longitudinal cross-section of the middle or right-most portion of a laminate.

Figure 4B:
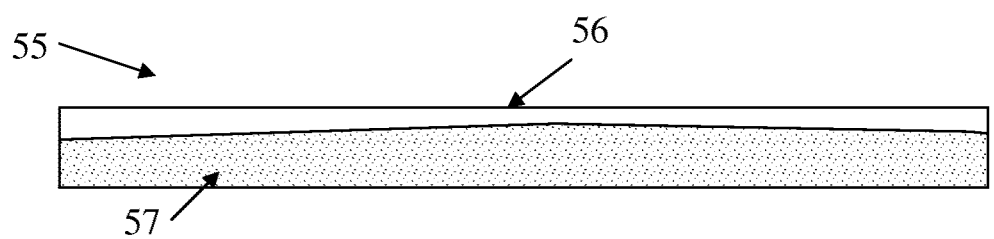

FIG. 4b depicts a laminate (55) having a non-uniform longitudinal cross-section. The shape of the longitudinal cross-section of the backing layer (56) and the reservoir layer (57) changes along the transverse width and length (linear axis) of the laminate. In this laminate, the reservoir layer (57) comprises a major portion of the laminate.

Figure 4C:
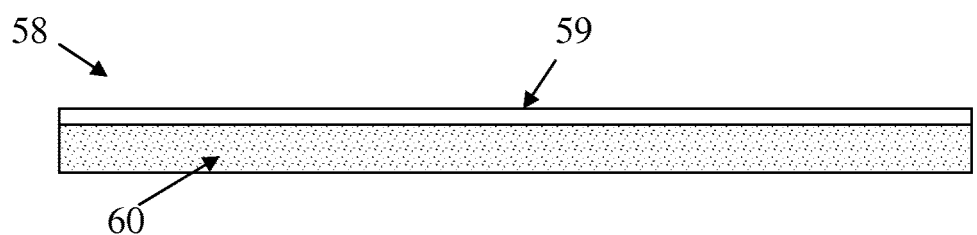
FIG. 4c depicts a longitudinal cross-sectional elevation of the laminate of FIG. 2a which has a uniform longitudinal cross-section across the transverse width of the laminate.

FIG. 4c depicts a laminate (59) having a uniform longitudinal cross-section. The longitudinal cross-section of the backing layer (59) and the reservoir layer (60) does not change substantially across the transverse width or length (linear axis) of the laminate.

Figure 5:
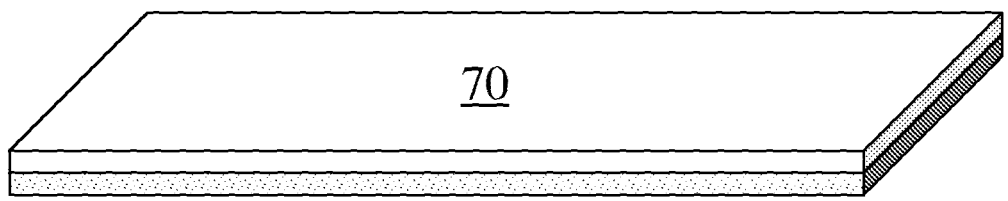
FIG. 5 depicts a perspective view of the laminate having a uniform transverse cross-section and a uniform longitudinal cross-section.

FIG. 5 depicts a bi-layered laminate (70) having a uniform transverse cross-section and a uniform longitudinal cross section. Even though the laminate is a flat sheet, it can still be shaped otherwise as described herein while retaining the uniformity of its cross-sections.

The extrudate prepared as detailed herein provides active agent dispersed within a thermoplastic bioadhesive matrix comprising a thermoplastic polymer, bioadhesive polymer, and/or water soluble and/or erodible polymer. The thermoplastic polymer is considered a thermal binder, a pressure softenable binder, or a combination thereof.

Exemplary thermal binders include: polyethylene oxide; polypropylene oxide; polyvinylpyrrolidone; polyvinylpyrrolidone-co-vinylacetate; acrylate and methacrylate copolymers; polyethylene; polycaprolactone; polyethylene-co-polypropylene; alkylcelluloses such as methylcellulose; hydroxyalkylcelluloses such as hydroxymethylcellulose, hydroxyethylcellulose, hydroxypropylcellulose, and hydroxybutylcellulose; hydroxyalkyl alkylcelluloses such as hydroxyethyl methylcellulose and hydroxypropyl methylcellulose; starches, pectins; PLA and PLGA, polyesters (shellac), wax such as carnauba wax, beeswax; polysaccharides such as cellulose, tragacanth, gum arabic, guar gum, and xanthan gum.

PEO can be used as the matrix-forming thermoplastic material. A specific embodiment of the binder is poly(ethylene oxide) (PEO), which can be purchased commercially from companies such as the Dow Chemical Company and Sumitomo Seika, which market PEO exemplary grades with an average molecular weight from about 100,000 to about 8,000,000. Some of the grades of PEO that are suitable for use in this invention are described in the tables below, which differentiate the grades according to their approximate molecular weights and solution viscosity.

| Trade Name | Approximate Molecular Weight | Viscosity Range Aqueous Solution at 25° C., mPa · s |
| --- | --- | --- |
| WSR N-10 | 100,000 | 30-50 (5% solution) |
| PEO-1Z | 150,000-400,000 | 50-200 (5% solution) |
| WSR N-80 | 200,000 | 55-90 (5% solution) |
| WSR N-750 | 300,000 | 600-1,200 (5% solution) |
| WSR N-3000 | 400,000 | 2250-4500 (5% solution) |
| WSR-205 | 600,000 | 4,500-8,800 (5% solution) |
| PEO-3Z | 600,000-1,100,000 | 2,500-5,500 (5% solution) |
| WSR-1105 | 900,000 | 8,800-17,600 (5% solution) |
| WSR N-12K | 1,000,000 | 400-800 (2% solution) |
| PEO-8Z | 1,700,000-2,200,000 | 20-70 (0.5% solution) |
| WSR N-60K | 2,000,000 | 2,000-4,000 (2% solution) |
| PEO-15Z | 3,300,000-3,800,000 | 130-250 (0.5% solution) |
| WSR-301, UCARFLOC Polymer 300 | 4,000,000 | 1,650-5,500 (1% solution) |
| PEO-18Z | 4,300,000-4,800,000 | 250-430 (0.5% solution) |
| WSR Coagulant, UCARFLOC Polymer 302 | 5,000,000 | 5,500-7,500 (1% solution) |
| WSR-303, UCARFLOC Polymer 304 | 7,000,000 | 7,500-10,000 (1% solution) |
| PEO-27 | 6,000,000-8,000,000 | 600-800 (0.5% solution) |
| WSR-308, UCARFLOC Polymer 309 | 8,000,000 | 10,000-15,000 (1% solution) |

In general, any PEO material described herein or any known PEO having the characteristics of a PEO material as described herein can be used.

In one embodiment, the term "PEO Grade 1" is taken to mean a polyethylene oxide with a solution viscosity in the range of 12-8800 mPa·s at 25° C. in a 5% solution or approximate molecular weight range from 100,000-600,000. Examples of Grade 1 PEOs are listed in the table above and include POLYOX WSR N-10, WSR N-80, WSR N-750, WSR N-3000, WSR N-205 or equivalents thereof.

In one embodiment, the term "PEO Grade 2" is taken to mean a polyethylene oxide with a solution viscosity in the range of 8800 mPa·s at 25° C. in a 5% solution to 4000 mPa·s at 25° C. in a 2% solution or approximate molecular weight range from 900,000-2,000,000. Examples of Grade 2 PEOs are listed in the table above and include POLYOX WSR N-1105, WSR N-12K, WSR N-60, or equivalents thereof.

In one embodiment, the term "PEO Grade 3" is taken to mean a polyethylene oxide with a solution viscosity in the range of 1650-15,000 mPa·s at 25° C. in a 1% solution or approximate molecular weight range from 4,000,000-8,000,000. Examples of Grade 1 PEOs are listed in the table above and include POLYOX WSR 301, WSR Coagulant, WSR 303, WSR 308, or equivalents thereof.

PEO Grade 1, PEO Grade 2 and/or PEO Grade 3 can occur in the drug reservoir layer, the inert backing layer or both layers. In the embodiment wherein a particular grade of PEO occurs in the reservoir layer and the inert backing layer, that grade of PEO is independently selected at each occurrence from its respective definition. In other words, if PEO Grade 1 occurs in the reservoir layer and the backing layer, then it will be selected at each occurrence from the above-specified group for PEO Grade 1. Likewise for PEO Grade 2 and PEO Grade 3.

When three grades of PEO are included in the same layer, PEO Grade 3 has a higher viscosity than PEO Grade 2, which has a higher viscosity than PEO Grade 1. When two grades of PEO are included in the same formulation, there are several possible combinations: a) PEO Grade 3+PEO Grade 2, wherein PEO Grade 3 has a higher viscosity than PEO Grade 2; b) PEO Grade 3+PEO Grade 1, wherein PEO Grade 3 has a higher viscosity than PEO Grade 1; and c) PEO Grade 2+PEO Grade 1, wherein PEO Grade 2 has a higher viscosity than PEO Grade 1.

When three different grades of PEO are present, the amount of each ranges between 0 to 99.5% wt. of the layer. In specific embodiments of such a composition, the amount of PEO Grade 1 can be from 5 to 50% by wt. of the layer, such as 5%, 10%, 26.85%, 27.9%, 23.67%, 32.9%, 36.01%, 34%, 38.16%, 33.86% of the layer; the amount of PEO Grade 2 can be from 5 to 50% by wt. of the layer, such as 5%, 22.18%, 21.16%, 26.16%, 20.36%, 28.64%, 27%, 30.35%, 14.96%, 15.91%, 18.36%, 18.86%, 19.36%, 7.5% of the layer; and the amount of PEO Grade 3 can be from 5 to 50% by wt. of the layer, such as 13.79%, 16.29%, 16.79%, 17.44%, 19.1%, 18%, 20.24%, 29.93%, 31.83%, 36.5%, 45% wt. of the layer.

The total amount of PEO present can range from about 10% to about 70% by wt. of the reservoir layer and 0 to about 60% by wt. of the backing layer.

When any type or class of material is present in both the reservoir and the backing layer, it will be independently selected at each occurrence from the list of suitable materials described herein or known to the artisan in the field of pharmaceutics. For example, if PEO is present in both the reservoir layer and the backing layer, the grade or grades of PEO used in reservoir layer will be selected at each occurrence independently of the grade or grades of PEO used in the backing layer.

Suitable thermal binders that may or may not require a plasticizer include, for example, Eudragit™ RS PO, Eudragit™ S100, Kollidon SR (poly(vinyl acetate)-co-poly (vinylpyrrolidone) copolymer), Ethocel™ (ethylcellulose), HPC (hydroxypropylcellulose), cellulose acetate butyrate, poly(vinylpyrrolidone) (PVP), poly(ethylene glycol) (PEG), poly(ethylene oxide) (PEO), poly(vinyl alcohol) (PVA), hydroxypropyl methylcellulose (HPMC), ethylcellulose (EC), hydroxyethylcellulose (HEC), sodium carboxymethylcellulose (CMC), dimethylaminoethyl methacrylate-methacrylic acid ester copolymer, ethylacrylate-methylmethacrylate copolymer (GA-MMA), C-5 or 60 SH-50 (Shin-Etsu Chemical Corp.), cellulose acetate phthalate (CAP), cellulose acetate trimelletate (CAT), polyesters (shellac), waxes (carnauba wax, beeswax), poly(vinyl acetate) phthalate (PVAP), hydroxypropylmethylcellulose phthalate (HPMCP), poly (methacrylate ethylacrylate) (1:1) copolymer (MA-EA), poly (methacrylate methylmethacrylate) (1:1) copolymer (MA-MMA), poly(methacrylate methylmethacrylate) (1:2) copolymer, Eudragit L100 (MA-EA, 1:1), Eudragit L-100-55 (MA-EA, 1:1), hydroxypropylmethylcellulose acetate succinate (HPMCAS), Coateric (PVAP), polycaprolactone, starches, pectins; polysaccharides such as cellulose, tragacanth, gum arabic, guar gum, sugars and xanthan gum.

Some of the above-noted binders are bioadhesive alkaline thermoplastic polymers.

PEO is considered a bioadhesive polymer, since it adheres to a biological surface (e.g. skin, mucosa). However, a reservoir layer made with PEO as the major thermoplastic matrix-forming polymer is not bioadhesive per se in the absence of water. PEO requires activation with moisture in order to adhere to the surface. During use, a PEO-based reservoir layer is moistened either with water present at the site of administration (for example water from saliva or a mucosal surface) or with other water. For this reason, PEO is termed a moisture-activated bioadhesive polymer.

In one embodiment, PEO is neutralized or moderately acidified with an acidic component. The polymer is neutralized by wet granulating it with the other materials, such as POLOXAMER®, to be included in the matrix, and the acidic component, such as citric acid and/or CARBOPOL®. Wet granulation is conducted with water (or buffer) or an aqueous alcohol solution. After this excipient mixture has been prepared, it is optionally dried and then blended with the testosterone followed by hot-melt extrusion of the entire mixture.

The acidic component can be mixed with the PEO as a liquid or solid. For example, the acidic component may be dissolved, suspended or wet with the aqueous medium used for wet granulation. Alternatively, the acidic component can be added in solid form.

In one embodiment, the acidic component will dissolve during the wet granulation step. In another embodiment, it will not. For example, when the acidic component is an acidic polymer, it may or may not dissolve during wet granulation. The acidic component can at least become hydrated (or wet) with the aqueous medium.

Other polymeric materials that can be included in the matrix include cellulosic polymers including HPMC, HPC, HEC, methylcellulose; polyvinyl alcohol, polyvinylpyrrolidone, polyvinylpyrrolidone-co-vinyl acetate and other polymers approved for pharmaceutical use known to those of ordinary skill in the art.

The bioadhesive thermoplastic matrix can further comprise other materials, in particular other polymers such as KLUCEL (hydroxypropylcellulose), CARBOPOL, polycarbophil, GANTREZ, Poloxamer, and combinations thereof. The product literature for CARBOPOL® indicates that aqueous solutions containing it have a pH in the range of 2.5-4.0, meaning it is an acidic polymer, and it is a bioadhesive polymer. GANTREZ® is a copolymer of methyl vinyl ether and maleic anhydride, and its solution pH will depend upon the form in which it is provided. GANTREZ® MS is a mixed calcium and sodium salt of the polymer having a solution pH between 5.5-7.0. GANTREZ® is a bioadhesive polymer but not a thermoplastic polymer. The product literature for polycarbophil, high molecular weight, cross-linked, acrylic acid-based polymers, indicates that aqueous solutions containing it have a pH less than 4.0, meaning it is an acidic polymer, and it is a bioadhesive polymer. Poloxamer 407 is a block copolymer of ethylene glycol and propylene glycol and according to the product literature it has a solution pH of 6.0-7.4. Poloxamer is not considered a bioadhesive polymer.

An extrudate composed of PEO and Poloxamer can form a homogeneous polymer matrix when melt extruded at 100° C. Compositions further comprising HPMC, PVA, or SLS can be made.

A single polymer or a combination of polymers can serve to give the matrix its thermoplastic and bioadhesive properties. Accordingly, the thermoplastic bioadhesive matrix of the invention can include a combination of materials, some of which may or may not be water soluble and/or erodible, bioadhesive, or thermoplastic. It is only important that the matrix retain its bioadhesive thermoplastic nature prior to hot-melt extrusion and retain its bioadhesive nature after hot-melt extrusion.

The matrix can contain one or more bioadhesive polymers, and/or one or more thermoplastic polymers. In one embodiment, the thermoplastic polymer is also the bioadhesive polymer.

The hot-melt extrusion equipment is typically a single or twin-screw apparatus, but can be composed of more than two screw elements. A typical hot-melt extrusion apparatus contains a mixing/conveying zone, a heating/melting zone, and a pumping zone in succession up to the orifice. In the mixing/conveying zone, the powder blends are mixed and aggregates are reduced to primary particles by the shear force between the screw elements and the barrel. In the heating/melting zone, the temperature is at or above the melting point or glass transition temperature of the thermal binder or binders in the blend such that the conveying solids become molten as they pass through the zone. A thermal binder in this context describes an inert excipient, typically a polymer that is sufficiently solid at ambient temperature, but becomes molten, softened or semi-liquid when exposed to elevated heat or pressure. The thermal binder acts as the matrix in which the active or actives and other functional ingredients are dispersed, or the adhesive with which they are bound such that a continuous composite is formed at the outlet orifice. Once in a molten state, the homogenized blend is pumped to the orifice through another heating zone that maintains the molten state of the blend. At the orifice, the molten blend can be formed into strands, cylinders or films. The extrudate that exits is then solidified typically by an air-cooling process. The extrudate can be a single layer or it can be a coextruded laminate or a bi-layered, tri-layered or other multi-layered laminate formed by laminating two or more layers together. Once solidified, the extrudate may then be further processed to form pellets, spheres, fine powder, tablets, and the like. An example of a single screw apparatus similar to the description above is the Randcastle Taskmaster, model 1 inch, 36:1.

Temperature can be an important process variable to consider for the hot-melt extrusion. The composition can be HME at any temperature desired provided it does not result in excessive degradation of the composition or any of it components. The examples below detail some suitable operating ranges for the barrel temperature of the various stages of a multi-stage screw extruder.

Other process variables such as feed rate and screw speed are optimized to provide adequate shear and mixing. The effect of feed rate and screw speed on such dependent variables as the level of shear and mixing inside the extruder depends heavily on the design of the equipment and namely the screw elements. Generally, increasing the screw speed will increase the shear forces between the screw element and the barrel wall, thereby allowing for more rigorous mixing and a greater extent of particle disaggregation. Decreasing the feed rate (non-flood feeding) will generally allow for more complete mixing and particle disaggregation due a reduction in the amount of material within the extruder. Reducing the amount of material will in turn also increase the shear forces the material is subjected to due to a decrease in the effective channel depth.

The order or ways in which the components of a formulation are fed to the extruder should be considered. One method is to pre-blend all formulation components before being fed to the extruder. This can be done by any traditional mixing or blending technique. Alternatively, formulation components may be fed individually if done simultaneously, and given that there is adequate mixing of the formulation components in the mixing/conveying zone of the extruder. For example, the drug is mixed with the excipient composition after formation of the excipient composition. The blend is then hot-melt extruded. Furthermore, components other than the base polymers may also be fed downstream of the initial feed port to reduce their residence time in the extruder given that there is adequate mixing of the formulation components before and in the last mixing zone. For example, an excipient blend may be fed at the initial feed port and a heat sensitive component may be fed prior to the last zone to minimize the time of heat exposure. Additionally, a solid non-melting component that significantly increases the melt viscosity may be fed downstream to reduce the amount of energy required to rotate the extruder screw.

Another suitable process employs a preformed excipient mixture, which can be prepared by a variety of different methods. One particular method is wet or dry granulation. In one embodiment, the excipient mixture is prepared by wet granulating the bioadhesive thermoplastic polymer and one or more other excipients, in the presence of an aqueous medium. The excipient mixture is optionally dried after wet granulation. Then, the dry or wet excipient mixture is mixed with drug, and optionally one or more other excipients, to form a blend that is then hot-melt extruded. The aqueous medium can be added in portions or in a bolus. The aqueous medium can be water, buffer or an aqueous alcohol solution. The preformed excipient mixture can also be formed by hot-melt extruding a physical mixture of the bioadhesive thermoplastic polymer, an acidic component and, optionally, one or more other excipients to form an extrudate that is then ground, milled, pelletized, beaded or pulverized to form the excipient mixture. Subsequently, the preformed excipient mixture is mixed with the testosterone, and optionally one or more other excipients, and hot-melt extruded to form the drug reservoir layer.

The HME composition of the invention is made according to a process as described herein. Exemplary formulations and processes for their preparation are detailed in the examples below.

General methods for hot-melt extrusion of the multi-layered laminate are detailed herein and in the examples below.

When wet granulation is employed to prepare the excipient mixture, an aqueous medium is used. Exemplary aqueous medium includes water, buffer, or water (or buffer) containing organic solvent. In one embodiment, the organic solvent is water miscible. Suitable water miscible solvents include methanol, ethanol, propanol, iso-propanol, benzyl alcohol, cyclomethicone, glycerin, propylene glycol, low molecular weight polyethylene glycol, simethicone, and others known to those of ordinary skill in the art.

Wet granulation technique (water addition rate, acidification time and water content) may have an impact upon the stability of the active agent. The rate of water addition can be changed by using "BOLUS" loading versus "SERIAL" addition (sequential addition of portions).

The total quantity of water in the excipients may have an impact upon active agent stability in the formulation. A reduction in major impurities may be observed using higher water loading, for example 7.5% water instead of 5% water. Even so, a water loading of up to 98% can be used provided the extruder is equipped to handle the increased amounts of steam formed using feed mixtures having high water content.

Instead of water or buffer alone, the aqueous medium for wet granulation can be a hydroalcoholic granulation solution. The ratio of water to water miscible solvent (in particular alcohol) in the granulation solution can range from 5:95 to 95:5.

Figure 7:
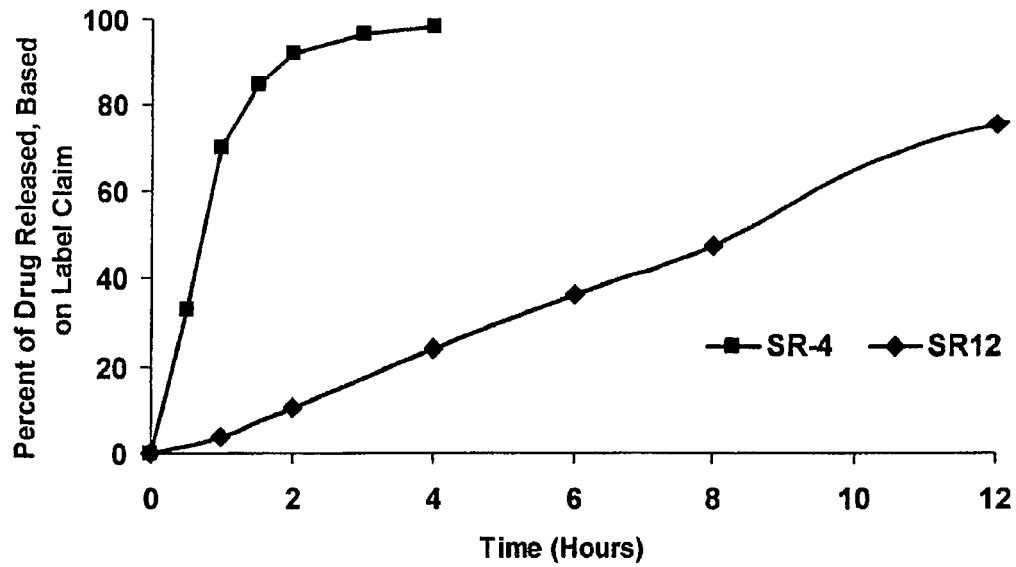
FIG. 7 depicts in vitro release profiles for Formulations SR4 and SR12.

The weight of an exemplary unit dose (SR4, Examples 3 and 9, FIG. 7) averages 109.5 mg. For example, a unit dose of laminate can have an average length of 20.77 mm, an average width of 11.61 mm and an average thickness of 0.42 mm thus providing an average surface area of 241 mm$^2$ for the exposed reservoir surface and a surface area to dose ratio of 12.1 mm$^2$/mg testosterone based upon the exposed reservoir surface. As used herein, the term "exposed reservoir surface" means that surface of the reservoir layer that is adapted for contact to a subject during transdermal administration.

The exemplary unit dose (SR12, Examples 3 and 9, FIG. 7) provides an extended release of testosterone, wherein the total amount of time during which testosterone is released can be varied according to the composition of the reservoir layer. The laminate of the invention can be adapted to release drug over a total approximate 4-hour (SR4 laminate) or 12-hr (SR12 laminate) period, respectively, after initial exposure to an aqueous environment. In other words, an SR4 laminate can release active agent, such as testosterone, substantially continuously over an extended period of about four hours once the laminate has been placed in the aqueous assay medium. An SR12 laminate can release testosterone substantially continuously over an extended period of about twelve hours once the laminate has been placed in the aqueous assay medium.

The in vivo performance of the SR4 and SR12 formulations can be evaluated by administration of each laminate to the buccal mucosa of different subjects. For example, an in vivo single center, 3-period crossover study can be conducted in a predetermined number of otherwise healthy hypogonadal males. Each subject would receive a single dose of one or more buccal film formulations. Each dose would be separated from the others by at least 7 days to wash out. Then, pharmacokinetic data for each participant in the study would be obtained and analyzed. Useful pharmacokinetic data would include, by way of example and without limitation, $AUC_{(0-24)}$ (measured as ng·h/dL), Cmax (measured as ng/dL), and Tmax (measured in hours from the time of administration). It would be useful to include a known pharmaceutical formulation as a control in the study to serve as a basis for comparison of the laminate unit doses of the invention.

The in vitro release profile for the laminates Formulas A, B, C, and D, which release testosterone over a total about 12-hr to 18-hr period after initial exposure to an aqueous environment, was evaluated. The laminates release testosterone substantially continuously over an extended period of about twelve to eighteen hours once the laminate has been placed in the aqueous assay medium. The Formulations A-D comprise a different backing layer than do the SR4 and SR12 formulations. The backing layer for formulations A-D was prepared by melt extrusion and applied to the drug reservoir using an adhesive. The dimensions and surface area of the doses also differed (Example 9).

The in vivo performance of the Formulations A-D was evaluated by administration of each laminate to the buccal mucosa of different subjects. An in vivo study was a single center, 4 way crossover study in 12 otherwise healthy hypogonadal males. Each subject received a single unit dose of 4 testosterone buccal film formulations (A, B, C, & D). Each dose was separated from the others by at least 72 hours to wash out. Pharmacokinetic data is presented in the following tables.

| $AUC_{(0-24)}$ Pharmacokinetic Summary (Baseline Adjusted, ng·h/dL) | | | | | | |
|---|---|---|---|---|---|---|
| Treatment | N | Mean | Geometric Mean | SD | $CV_b$ (%) | Min | Max |
| A | 12 | 10462 | 9838 | 3743 | 38.4% | 5667 | 16417 |
| B | 12 | 11081 | 9929 | 5409 | 52.1% | 5392 | 19946 |
| C | 12 | 11057 | 10036 | 4522 | 53.2% | 2996 | 18598 |
| D | 12 | 11015 | 10652 | 2905 | 28.0% | 6532 | 15694 |

| $AUC_{(0-24)}$ Treatment Comparisons & 95% Confidence Intervals (Baseline Adjusted) | | |
|---|---|---|
| Comparison | Ratio | 95% Confidence Interval |
| A vs B | 99.1% | (81.2%, 120.9%) |
| A vs C | 98.0% | (80.3%, 119.6%) |
| A vs D | 92.4% | (75.7%, 112.7%) |
| B vs C | 98.9% | (81.1%, 120.7%) |
| B vs D | 93.2% | (76.4%, 113.7%) |
| C vs D | 94.2% | (77.2%, 115.0%) |

| Cmax Pharmacokinetic Summary (Baseline Adjusted, ng/dL) | | | | | | | |
|---|---|---|---|---|---|---|---|
| Treatment | N | Mean | Geometric Mean | SD | $CV_b$ (%) | Min | Max |
| A | 12 | 1526 | 1435 | 636 | 35.5% | 920 | 3177 |
| B | 12 | 1370 | 1310 | 411 | 32.7% | 759 | 1973 |
| C | 12 | 1563 | 1476 | 561 | 36.3% | 902 | 2592 |
| D | 12 | 1378 | 1343 | 332 | 23.9% | 1019 | 2035 |

| Cmax Treatment Comparisons & 95% Confidence Intervals (Baseline Adjusted) | | |
|---|---|---|
| Comparison | Ratio | 95% Confidence Interval |
| A vs B | 109.5% | (89.9%, 133.4%) |
| A vs C | 97.3% | (79.8%, 118.5%) |
| A vs D | 106.8% | (87.7%, 130.1%) |
| B vs C | 88.8% | (72.9%, 108.2%) |
| B vs D | 97.6% | (80.1%, 118.8%) |
| C vs D | 109.8% | (90.2%, 133.8%) |

Figure 8:
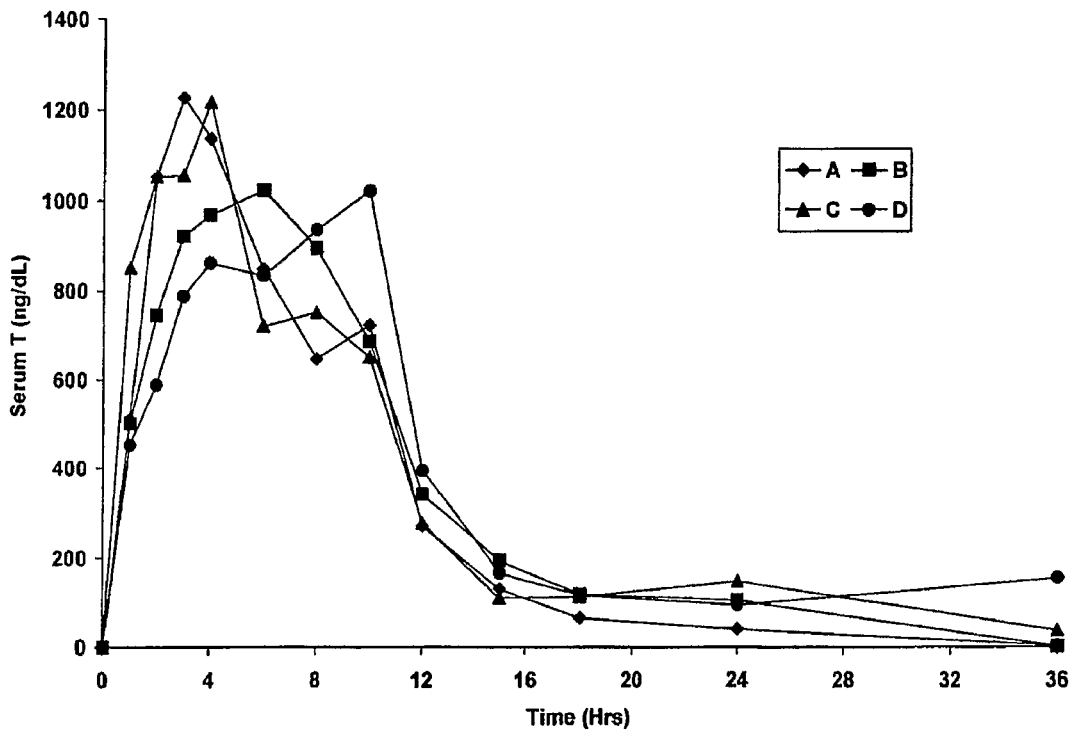
FIG. 8 depicts in vivo plasma profiles for Formulations A-D.

FIG. 8 depicts the plasma profile obtained when the laminates Formulation A-D were administered buccally. Formulations A, B and D provided a bimodal (biphasic) plasma concentration profile for testosterone. In these particular formulations, the plasma concentration of testosterone peaked twice: 1) Formulation A exhibited a first plasma concentration peak of 1200-1300 ng/dL at 2-4 hours after administration and a second plasma concentration peak of 600-800 ng/dL at 8-12 hours after administration; 2) Formulation C exhibited a first plasma concentration peak of 1200-1300 ng/dL at 3-5 hours after administration and a second plasma concentration peak of 600-800 ng/dL at 6-10 hours after administration; and 3) Formulation D exhibited a first plasma concentration peak of 800-1000 ng/dL at 2-6 hours after administration and a second plasma concentration peak of 1000-1100 ng/dL at 8-12 hours after administration. On the other hand, Formulation B provided a mono-modal (monophasic) plasma concentration profile having a peak plasma concentration 900-1100 ng of testosterone/dL at about 4-8 hours after administration.

Key differences between the Formulations A-D versus the SR4 and SR12 laminates are: Formulations A-D comprise two to three different grades of PEO (Polyethylene Oxide); they exclude polycarbophil; and Formulations A-D are processed at much higher temperatures. The dose for all formulations was 20 mg, except for formulation D, which was 15 mg. The dimensions, surface area and thickness varied as described above.

Figure 9:
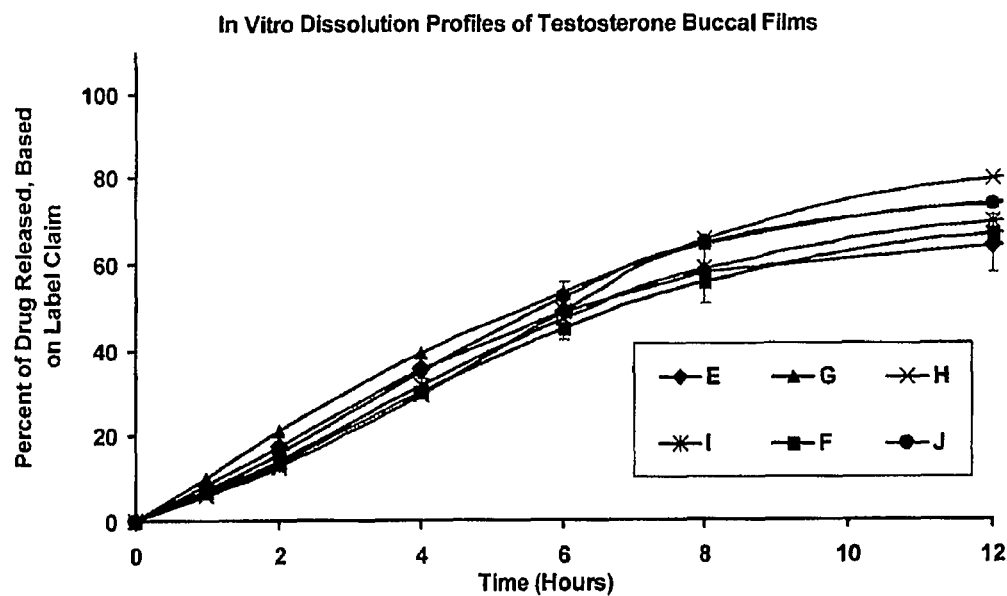
FIG. 9 depicts in vitro release profiles for Formulations E-J.

The laminate Formulations E-J are prepared according to Example 3 and the in vitro (FIG. 9) and in vivo (FIG. 10) performance thereof is evaluated as described herein. The laminates provide an extended release of testosterone, wherein the total amount of time during which testosterone is released can be varied according to the composition of the reservoir layer. The laminates, Formulas E-J, release testosterone over a total about 12-hr to 24-hr period after initial exposure to an aqueous environment. The Formulations E-J differ amongst themselves in the amount of each grade of PEO included, the testosterone dose and the film dimensions (length, width, surface area, and thickness) as described below.

The Formulations E-J differ from Formulations A-D in the amount of each grade of PEO included and in the presence of Carbopol in each of Formulations E-J. Moreover, Formulations E-J are extruded at higher temperatures than Formulations A-D. Also, the Formulations E-J comprise a different backing layer than do the SR4 and SR12 formulations and the Formulations A-D. The backing film was modified using Eudragit RS PO in place of Eudragit E PO to reduce permeability and provide an improved barrier. This backing film was applied to the drug reservoir using an adhesive. In other words, each laminate releases testosterone substantially continuously over an extended period of about 24 hours once the laminate has been placed in the aqueous assay medium. The in vivo performance (FIG. 10) of the Formulations E-J was evaluated by administration of each laminate to the buccal mucosa of different subjects as described herein.

The Formulations E-J can provide a Cmax of less than 900 ng/dL with a Tmax at about 4 to 8 hours after buccal administration. These formulations can also provide a testosterone plasma level between about 300 and about 900 ng/dL throughout the period of about 1 to 15 hours, or about 1 to 12 hours, after buccal administration to a subject.

Figure 10:
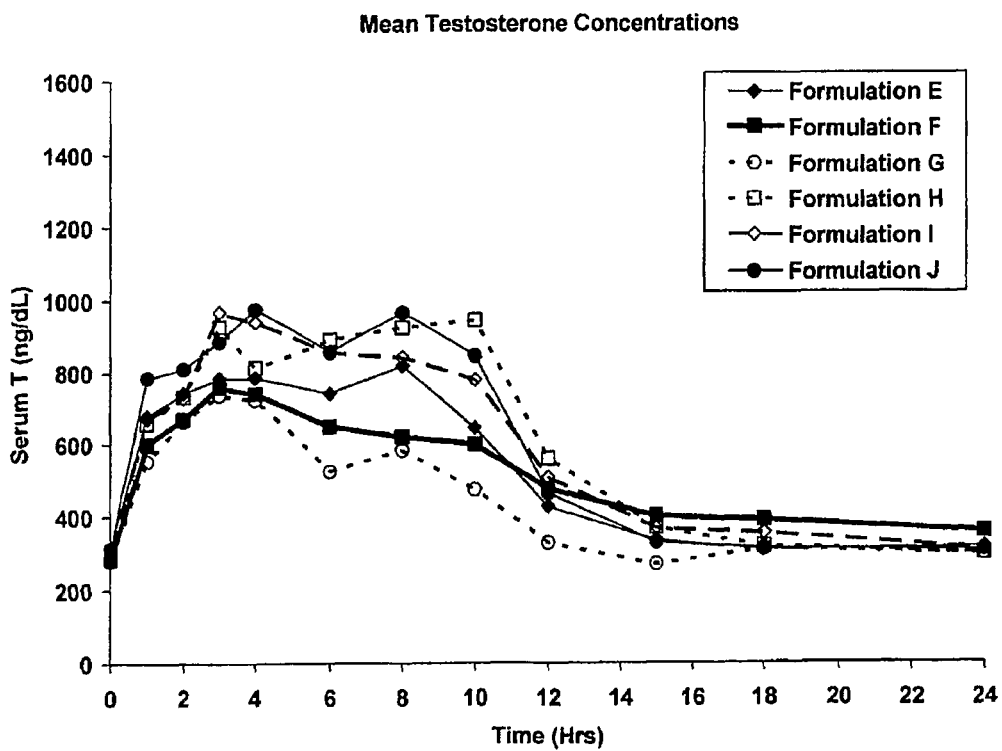
FIG. 10 depicts in vivo plasma profiles for Formulations E-J.

FIG. 10 depicts the plasma profile obtained when the laminates Formulation E-J were administered buccally. Each formulation provided a bimodal plasma concentration profile for testosterone. In these particular formulations, the plasma concentration of testosterone peaked twice: 1) Formulation E exhibited a first plasma concentration peak of 700-900 ng/dL at 2-6 hours after administration and a second plasma concentration peak of 700-900 ng/dL at 6-10 hours after administration; 2) Formulation F exhibited a first plasma concentration peak of 600-800 ng/dL at 2-5 hours after administration and a second plasma concentration peak of 500-700 ng/dL at 8-12 hours after administration; 3) Formulation G exhibited a first plasma concentration peak of 600-800 ng/dL at 2-6 hours after administration and a second plasma concentration peak of 500-700 ng/dL at 6-10 hours after administration; 4) Formulation H exhibited a first plasma concentration peak of 800-1000 ng/dL at 2-4 hours after administration and a second plasma concentration peak of 800-1000 ng/dL at 6-11 hours after administration; 5) Formulation I exhibited a first plasma concentration peak of 900-1000 ng/dL at 2-6 hours after administration and a second plasma concentration peak of 700-900 ng/dL at 6-11 hours after administration; and 6) Formulation J exhibited a first plasma concentration peak of 900-1100 ng/dL at 2-6 hours after administration and a second plasma concentration peak of 900-1100 ng/dL at 6-10 hours after administration.

The Formulation K can provide a Cmax of less than 900 ng/dL with a Tmax at about 3 to 9 hours after buccal administration. This formulation can also provide a testosterone plasma level between about 300 and about 900 ng/dL throughout the period of about 0.5 to 15 hours, or about 1 to 12 hours, after buccal administration to a subject.

Figure 11:
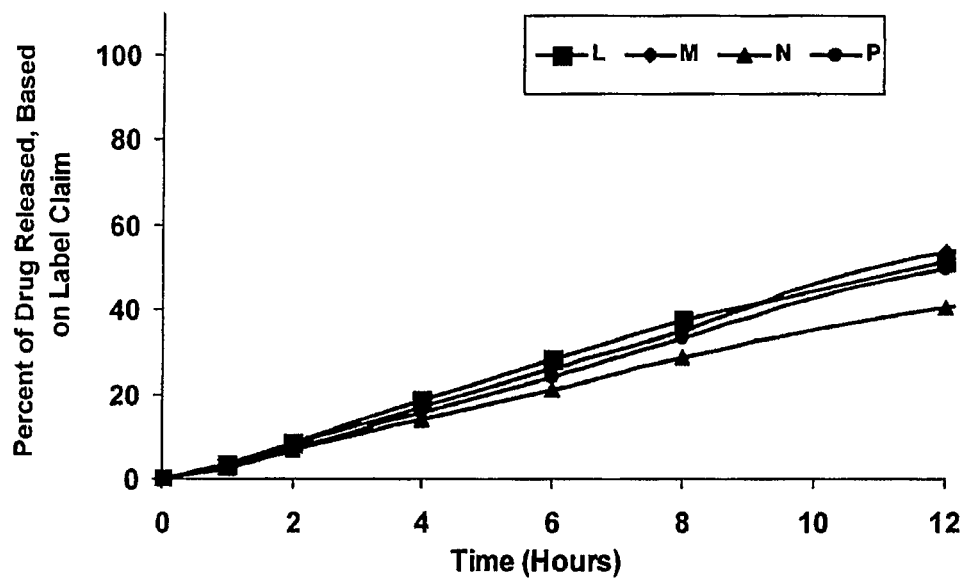
FIG. 11 depicts in vitro release profiles for Formulations L-P.

The laminate Formulations L-P were prepared according to Example 11 and their in vitro (FIG. 11) and in vivo (FIG. 12) performance were evaluated as described herein. The bi-layered laminates comprise a hot-melt extruded drug reservoir layer and a hot-melt extruded inert backing layer. The laminate provides an extended release of testosterone. FIG. 11 depicts the in vitro release profile for the laminate Formulations L-P, which release testosterone over a total about 18-hr to 24-hr period after initial exposure to an aqueous environment. The Formulations L-P differ from Formulations SR4 and SR12 in the amount of each grade of PEO included, the presence of poloxamer in the Formulations L-P, and in the presence of Carbopol (5% wt.) in the Formulations L-P as opposed to the presence of polycarbophil (2% wt., Formulation SR4 and SR12). Moreover, Formulations L-P are extruded at higher temperatures than Formulations SR4 and SR12. Also, Formulations L-P comprise a different backing layer than do the SR4 and SR12 formulations.

The Formulations L-P differ from Formulations A-D in the amount of each grade of PEO included, the presence of poloxamer in the Formulations L-P as opposed to its absence in Formulations A-D, and in the presence of Carbopol (5% wt.) as opposed to its absence (Formulation A-D). Also, Formulations L-P comprise a different backing layer than do the Formulations A-D. Formulations L-P were prepared using a coextrusion method in which the drug reservoir and the backing layer were prepared simultaneously in two different extruders and brought together in a common die (a dual manifold film die) thereby fusing the two layers together prior to exiting the die. Formulations L-P also had different dimensions as described below. In other words, each laminate releases testosterone substantially continuously over an extended period of about 24 hours once the laminate has been placed in the aqueous assay medium.

The in vivo performance of the Formulations L-P was evaluated by administration of the laminate to the buccal mucosa of different subjects. Subjects received a dose of Formulations L-P for seven consecutive days. Pharmacokinetic data is presented in the following tables.

Day 1 AUC$_{(0-24)}$ Pharmacokinetic Summary ($^{ng \cdot h}/_{dL}$)

| Treatment | N | Mean | Geometric Mean | SD | CV$_b$ (%) | Min | Max |
|---|---|---|---|---|---|---|---|
| L | 6 | 16596 | 16215 | 3898.1 | 24.0 | 11865 | 21555 |
| M | 6 | 17948 | 17817 | 2328.1 | 13.5 | 14872 | 20088 |
| N | 6 | 17728 | 17182 | 4973.2 | 27.7 | 12459 | 26133 |
| P | 6 | 16403 | 16188 | 2790.0 | 18.4 | 11796 | 19715 |

Day 1 Baseline Adjusted AUC$_{(0-24)}$ Pharmacokinetic Summary ($^{ng \cdot h}/_{dL}$)

| Treatment | N | Mean | Geometric Mean | SD | CV$_b$ (%) | Min | Max |
|---|---|---|---|---|---|---|---|
| L | 6 | 6705 | 6108 | 3331.7 | 48.7 | 3600 | 12360 |
| M | 6 | 10368 | 9963 | 3372.0 | 30.8 | 7662 | 15821 |
| N | 6 | 8165 | 8061 | 1378.2 | 18.0 | 5929 | 10005 |
| P | 6 | 9530 | 8168 | 5486.1 | 70.0 | 3074 | 16388 |

Day 7 AUC$_{(0-24)}$ Pharmacokinetic Summary ($^{ng \cdot h}/_{dL}$)

| Treatment | N | Mean | Geometric Mean | SD | CV$_b$ (%) | Min | Max |
|---|---|---|---|---|---|---|---|
| L | 6 | 15238 | 14574 | 4634.9 | 34.9 | 8318 | 19935 |
| M | 6 | 14405 | 13741 | 5150 | 33.7 | 8923 | 23908 |
| N | 6 | 14577 | 13466 | 6807.8 | 45.5 | 7065 | 27437 |
| P | 6 | 13845 | 13771 | 1602.4 | 11.3 | 12138 | 16589 |

Day 7 Baseline Adjusted AUC$_{(0-24)}$ Pharmacokinetic Summary ($^{ng \cdot h}/_{dL}$)

| Treatment | N | Mean | Geometric Mean | SD | CV$_b$ (%) | Min | Max |
|---|---|---|---|---|---|---|---|
| L | 6 | 5774 | 4175 | 5138.0 | 114.8 | 8318 | 19935 |
| M | 6 | 7790 | 6366 | 6024.0 | 76.4 | 8923 | 23908 |
| N | 6 | 6215 | 5568 | 3027.5 | 56.4 | 3111 | 9719 |
| P | 6 | 7417 | 6499 | 4097.8 | 61.5 | 3621 | 13187 |

Day 7 Baseline Adjusted AUC$_{(0-24)}$ Treatment Comparisons & 95% Confidence Intervals

| Comparison | Ratio | 95% Confidence Interval |
|---|---|---|
| L vs M | 65.6% | (28.6%, 150.3%) |
| L vs N | 75.0% | (32.7%, 171.9%) |
| L vs P | 64.2% | (28.0%, 147.3%) |
| M vs N | 114.3% | (49.9%, 262.1%) |
| M vs P | 98.0% | (42.7%, 224.5%) |
| N vs P | 85.7% | (37.4%, 196.4) |

Day 1 C$_{max}$ ($^{ng}/_{dL}$) Pharmacokinetic Summary

| Treatment | N | Mean | Geometric Mean | SD | CV$_b$ (%) | Min | Max |
|---|---|---|---|---|---|---|---|
| L | 6 | 1233 | 1215 | 231.7 | 19.5 | 892 | 1557 |
| M | 6 | 1316 | 1305 | 181.6 | 14.2 | 1041 | 1562 |
| N | 6 | 1214 | 1190 | 251.0 | 23.1 | 785 | 1533 |
| P | 6 | 1644 | 1550 | 633.7 | 38.5 | 1026 | 2548 |

Day 1 Baseline Adjusted C$_{max}$ ($^{ng}/_{dL}$) Pharmacokinetic Summary

| Treatment | N | Mean | Geometric Mean | SD | CV$_b$ (%) | Min | Max |
|---|---|---|---|---|---|---|---|
| L | 6 | 810 | 753 | 333.8 | 45.1 | 379 | 1357 |
| M | 6 | 996 | 978 | 214.3 | 20.7 | 739 | 1385 |
| N | 6 | 812 | 793 | 180.9 | 24.9 | 541 | 977 |
| P | 6 | 1349 | 1179 | 778.7 | 61.2 | 635 | 2477 |

Day 7 C$_{max}$ ($^{ng}/_{dL}$) Pharmacokinetic Summary

| Treatment | N | Mean | Geometric Mean | SD | CV$_b$ (%) | Min | Max |
|---|---|---|---|---|---|---|---|
| L | 6 | 1384 | 1194 | 933.5 | 61.1 | 619 | 3192 |
| M | 6 | 1016 | 960 | 347.9 | 39.8 | 497 | 1457 |
| N | 6 | 1203 | 1186 | 209.4 | 18.7 | 864 | 1432 |
| P | 6 | 1416 | 1355 | 494.4 | 32.4 | 892 | 2353 |

Day 7 Baseline Adjusted C$_{max}$ ($^{ng}/_{dL}$) Pharmacokinetic Summary

| Treatment | N | Mean | Geometric Mean | SD | CV$_b$ (%) | Min | Max |
|---|---|---|---|---|---|---|---|
| L | 6 | 961 | 630 | 1063 | 122.5 | 221 | 2992 |
| M | 6 | 696 | 607 | 343.0 | 69.8 | 196 | 1173 |
| N | 6 | 801 | 776 | 218.4 | 28.3 | 525 | 1131 |
| P | 6 | 1121 | 996 | 607.9 | 57.8 | 444 | 2201 |

Day 7 Baseline Adjusted C$_{max}$ Treatment Comparisons & 95% Confidence Intervals

| Comparison | Ratio | 95% Confidence Interval |
|---|---|---|
| L vs M | 103.8% | (47.6%, 226.4%) |
| L vs N | 81.2% | (37.2%, 177.2%) |
| L vs P | 63.3% | (29.0%, 138.1%) |
| M vs N | 78.3% | (35.9%, 170.8%) |
| M vs P | 61.0% | (28.0%, 133.1%) |
| N vs P | 77.9% | (35.7%, 170.0%) |

Day 7 T$_{max}$ (hr) Pharmacokinetic Summary

| Treatment | N | Mean | SD | Min | Max |
|---|---|---|---|---|---|
| L | 6 | 8.5 | 3.6 | 3 | 12 |
| M | 6 | 8.0 | 5.6 | 2 | 15 |

-continued

Day 7 T$_{max}$ (hr) Pharmacokinetic Summary

| Treatment | N | Mean | SD | Min | Max |
|---|---|---|---|---|---|
| N | 6 | 10.0 | 7.3 | 4 | 24 |
| P | 6 | 6.7 | 2.4 | 4 | 10 |

The Formulations M & N provide a Cmax of less than 900 ng/dL with a Tmax at about 3 to 12 hours after buccal administration. These formulations also provide a testosterone plasma level between about 300 and about 900 ng/dL throughout the period of about 0.5 to 15 hours, or about 1 to 12 hours, after buccal administration to a subject. These formulations also provide a testosterone plasma level between about 600 and about 900 ng/dL throughout the period of about 2 to 14-15 hours after buccal administration to a subject. The Formulations L & P provide a Cmax of greater about 900 ng/dL to about 1200 ng/dL with a Tmax at about 7-9 hours after buccal administration. These formulations also provide a testosterone plasma level between about 300-1200 ng/dL throughout the period of about 1 to 12 hours after buccal administration to a subject.

Two formulations were prepared using differing Carbopol loads in which the target film thickness was 1.50 mm. These formulations were prepared by the hydroalcoholic wet granulation technique in which the Vitamin E and Vitamin E Succinate were emulsified with the Poloxamer. The in vitro dissolution profiles are presented in FIGS. 13a and 13b. The formulations differed in the amount of CARBOPOL polymer present: 12.5% (FIG. 13a); 15% (FIG. 13b). It can be concluded that increasing the dose thickness and the Carbopol content in the formulation retards the in vitro dissolution rate. The thickness of the reservoir layer can range from about 0.01 to about 20 mm or otherwise be manufactured in any size adapted for a particular purpose.

Figure 14B:
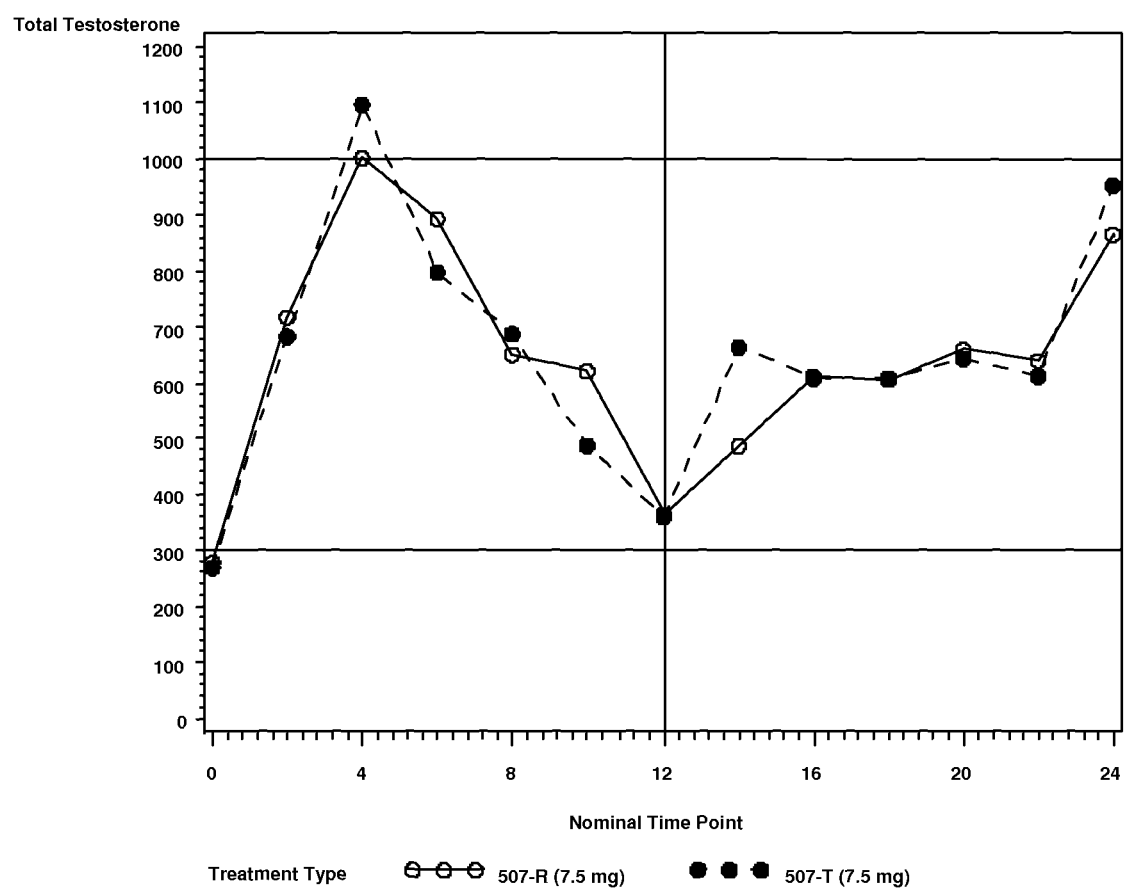
FIG. 14b depicts the testosterone mean plasma concentration after single day dosing for human subjects to which an extended release dosage form of the invention has been administered.

The laminate of the invention provides a reproducible plasma profile during single to multiple day administration. FIG. 14a depicts the mean plasma concentration for testosterone third day of administration of a thirteen day cycle in human subjects to which an extended release dosage form of the invention has been administered. The laminate was administered twice daily. FIG. 14b depicts the mean plasma concentration for testosterone during the first day administration of an eleven day administration cycle in human subjects to which an extended release dosage form of the invention has been administered. The laminate was administered twice daily.

For the laminates of FIGS. 14a and 14b, the overall daily plasma concentration profile was bimodal due to the twice daily administration of the laminate. In other words, the individual laminate provided a monomodal plasma profile when administered a single time (once daily) and provided a bimodal (biphasic) plasma profile when administered twice daily.

POLYOX (PEO) polymers contain residual calcium salts from the catalyst during synthesis. An acidic component or acidifying agent can be added to the PEO polymer to neutralize these alkaline materials prior to or during hot-melt extrusion. In one example, the acidic component was added in liquid form to the granulation mass or the granulation liquid medium. The total acidic component is present in an amount to sufficient to neutralize alkaline species present in the matrix. In other words, the total molar concentration of acidic component (or of total acidic groups) exceeds the molar concentration of total alkaline groups present in the composition. An acidic component can have 1, 2 or more moles of acidic groups per mole of acidic component.

Optionally, no wet granulation is required. In this embodiment, all materials to be added to a formulation are blended and then hot-melt extruded. This process, however, is only suitable when water soluble acidic components are used, as non-water soluble acidic components, such as CARBOPOL®, do not stabilize the film as well in this type of process. This because CARBOPOL® requires water for hydration in order to exert its acidic property. One way to overcome this disadvantage is to wet the non-water soluble acidic component prior to granulation with the bioadhesive alkaline thermoplastic polymer and extending the granulation time sufficiently to permit interaction of the non-water soluble acidic component with the bioadhesive alkaline thermoplastic polymer to form a neutral or moderately acidic excipient mixture.

As used herein, the term "acidic component" or "acidifying agent" means one or more acidic polymers (e.g. Carbopol®, Polycarbophil, polyacrylic acid), one or more inorganic acids (e.g. a mineral acid, (phosphoric acid, boric acid, hydrochloric acid, nitric acid, sulfuric acid, hydrobromic acid), one or more organic acids (non-polymeric carboxylic acid such as acetic acid, citric acid, tartaric acid, fumaric acid, succinic acid, amino acid, alpha-hydroxyl acid, ascorbic or adipic acid), or a combination thereof. An acidic component also includes the salt form or buffer of an acid, wherein the salt has solution pH of less than 7 or less than 6 when dissolved in water. The above-listed acidic components are merely illustrative and non-limiting. Any acidic component having a pKa of less than 7 or less than 6 would be suitable for use in the present invention. Specific embodiments include those wherein the acidic component is selected from the group consisting of: hydrochloric acid, phosphoric acid, citric acid and a combination thereof. An acidic component can be a combination of an acidic polymer and an organic acid, an acidic polymer and an inorganic acid, or an inorganic acid and an organic acid. An acidic component may also be a combination or two or more acidic polymers, two or more inorganic acids, or two or more organic acids. Exemplary formulations containing an acidic component in the reservoir layer are detailed below.

The solid dosage formulations of the invention can assume any shape or form known in the art of pharmaceutical sciences. The dosage form can be a sphere, tablet, bar, plate, paraboloid of revolution, ellipsoid of revolution or other one known to those of ordinary skill in the art. The solid dosage form can also include surface markings, cuttings, grooves, letters and/or numerals for the purposes of decoration, identification and/or other purposes.

The matrix and/or the additional functional excipients may be formulated as to provide a predetermined approximate release profile under predetermined conditions. The drug can be released according to a sustained, controlled, slow, pulsatile or extended drug release profile.

The pharmaceutical composition may deliver one or more active agents in an extended release manner, and mechanisms employed for such delivery can include active agent release that is pH-independent; diffusion or dissolution controlled; erosion controlled; pseudo-zero order (approximates zero-order release), zero-order, pseudo-first order (approximates first-order release), or first-order; or slow, or sustained release or otherwise controlled release. The in vitro release profile for the active agent can also be sigmoidal in shape, wherein the release profile comprises an initial slow release rate, followed by a middle faster release rate and a final slow release rate of active agent.

As used herein, the term "extended release" profile assumes the definition as widely recognized in the art of pharmaceutical sciences. An extended release dosage form will release drug at substantially constant rate over an extended period of time or a substantially constant amount of drug will be released incrementally over an extended period of time. An extended release tablet generally effects at least a two-fold reduction in dosing frequency as compared to the drug presented in a conventional dosage form (e.g., a solution or rapid releasing conventional solid dosage forms).

By "controlled release" is meant a release of an active agent to an environment over a period of about eight hours up to about 12 hours, 16 hours, 18 hours, 20 hours, a day, or more than a day. By "sustained release" is meant an extended release of an active agent to maintain a constant drug level in the blood or target tissue of a subject to which the device is administered. The term "controlled release", as regards to drug release, includes the terms "extended release", "prolonged release", "sustained release", or "slow release", as these terms are used in the pharmaceutical sciences. A controlled release can begin within a few minutes after administration or after expiration of a delay period (lag time) after administration.

A slow release dosage form is one that provides a slow rate of release of drug so that drug is released slowly and approximately continuously over a period of 3 hr, 6 hr, 12 hr, 18 hr, a day, 2 or more days, a week, or 2 or more weeks, for example.

A pseudo-first order release profile is one that approximates a first order release profile. A first order release profile characterizes the release profile of a dosage form that releases a constant percentage of an initial drug charge per unit time.

A pseudo-zero order release profile is one that approximates a zero-order release profile. A zero-order release profile characterizes the release profile of a dosage form that releases a constant amount of drug per unit time.

Suitable materials that can be used in preparing a thermoplastic matrix of the backing layer include, by way of example and without limitation, EUDRAGIT, ethylcellulose, polyethylene, cellulose acetate butyrate, cellulose acetate phthalate, wax, polyvinyl alcohol, polyvinyl acetate phthalate, polyester, shellac, other materials recognized in the chemical arts as having similar physical properties, or a combination thereof. The backing layer can be extruded as described herein. In one embodiment, the backing layer is impermeable to aqueous medium and drug. Non-limiting exemplary materials suitable for this type of backing layer include ethylcellulose, EUDRAGIT RS, wax, other materials recognized in the chemical arts as having similar physical properties, or a combination thereof. In another embodiment, it is semipermeable, meaning it is impermeable to drug and permeable to aqueous medium. Non-limiting exemplary materials suitable for this type of backing layer include PEO and ethylcellulose, PEO and EUDRAGIT RS, cellulose acetate and its derivatives, other materials recognized in the chemical arts as having similar physical properties, or a combination thereof. In still another embodiment, it is permeable to aqueous medium and drug. Non-limiting exemplary materials suitable for this type of backing layer include PEO and EUGRAGIT E, other materials recognized in the chemical arts as having similar physical properties, or a combination thereof.

Exemplary backing layers were made according to the examples below. In one embodiment, the hydrophobic composition of the backing layer is extruded separately from the hydrophilic composition of the reservoir layer. In one embodiment, the hydrophobic composition of the backing layer is coextruded with the hydrophilic composition of the reservoir layer. In one embodiment, the backing layer and reservoir layers are extruded individually and shortly thereafter heat-laminated, solvent-laminated or adhesive-laminated together during manufacture. In another embodiment, one layer is extruded onto the other layer which has been preformed, such as by extrusion or casting. In another embodiment, the backing layer and the reservoir layer are extruded separately and subsequently heat-laminated, solvent-laminated, or adhesive-laminated together The step of heat-catalyzed lamination is conducted by passing the backing layer and reservoir layer in contact with each other simultaneously through a laminator that applies pressure and optionally heat to the opposing layers. If the layers are sufficiently hot prior to lamination, they need not be heated again when placed in the laminator. If the layers are not sufficiently hot prior to lamination to permit suitable lamination, then they are heated just prior to and/or during lamination. The heat source can be located within or external to the laminator. The layers will generally be heated to about 100-170° C. or at least about 60° C. prior to and/or during lamination. The temperature for lamination will be below the temperature at which a layer degrades.

Solvent lamination can be achieved without heat by applying a fine mist of water or other suitable solvent or plasticizer two one or both of the opposing layers immediately prior to combining under pressure. This solvent lamination process is suitable when the reservoir layer and the backing layer each comprise a solvent-activated or plasticizer-activated adhesive material such as PEO.

The laminator can be a set of opposing rollers driven by one or two motors. The laminator will apply pressure to both layers during the lamination step. The contact pressure will generally be at least 40 pounds per linear inch or in the range of about 40-600 pounds per linear inch. The laminator rollers will be sufficiently rigid to withstand the forces exerted. The rollers may be hollow and internally baffled to allow for the use of a heat transfer fluid. The rollers may be comprised of a multiple metals and/or alloys providing suitable hardness and may contain suitable coatings to provide adequate release of the heated polymer. Suitable coatings for the rollers include, for example, Teflon®, Titanium Nitride, Chrome, and other material(s) used in the polymer industry for coating of heat laminators.

Although the invention includes a process and laminate wherein the reservoir layer and backing layer are laminated by way of heat-catalyzed lamination or coextrusion, an adhesive can be placed between the layers prior to heat lamination. The adhesive is a material known in the field of polymers as suitable to adhering the two layers together. The specific adhesive will vary according to the chemical composition, chemical properties, and physical properties of the reservoir layer and the backing layer. A non-limiting exemplary adhesive comprises KLUCEL and EUDRAGIT E100. For example, a bioadhesive reservoir layer comprising a hydrophilic HME matrix can be adhered to a non-bioadhesive backing layer comprising a hydrophobic HME matrix by applying an adhesive material at the interface between the two layers and subsequently pressing the two layers together. Weight or pressure can be applied to the layers optionally followed by drying to remove solvent, if present, from the adhesive.

The ratio of the thickness of the reservoir layer to the thickness of the backing layer can be varied as needed depending upon the performance desired for the laminate. In one embodiment, the ratio ranges from about 0.05:1 to about 5:1 or from about 2:1 to 4:1 or about 3:1.

When the backing layer and reservoir layer are laminated together by lamination or coextrusion, they will have at least one polymer in common. For example, if the reservoir layer contains PEO, then the backing layer could contain PEO as the polymer in common. The backing layer and reservoir layer can have one, two, three or more polymers in common. By so doing, the strength of interlayer adhesion between the backing layer and reservoir layer is increased as compared to a related laminate wherein the layers do not have a polymer in common. The greater the amount of polymer that the layers have in common, the greater the strength of interlayer adhesion. Likewise, the greater the number of polymers that the layers have in common, the greater the strength of interlayer adhesion.

In some embodiments, the backing layer and the reservoir layer each comprise at least 10% wt., or at least 95% wt. of the polymer(s) they have in common. For example, if the reservoir layer comprises 50% by wt. of PEO and the backing layer comprises 20% by wt. of PEO, then the layers each comprise at least 20% by wt. of PEO in common.

In some embodiments, the reservoir layer and the backing layer comprise no more than 55% by wt. or no more than 10% by wt. of polymer in common. In this way, the reservoir layer maintains its bioadhesiveness and the backing layer maintains its hydrophobicity and poor permeability.

Selection of the polymer for use in the individual layers of the laminate as well as for use as the at least one polymer in common can be done by determining the solubility parameter of the individual components of the compositions used to make the layers. The solubility parameters ($\delta$) can be used to predict the miscibility of drugs with excipients and polymers in a solid dispersion, such as the reservoir layer of the instant laminate. The method of Greenhalgh et al. (*Journal of Pharmaceutical Sciences*, (1999), 88(11): p. 1182-1190.) can be used to estimate the interactions between polar ($\delta_p$) and hydrogen bonding groups ($\delta_h$) significantly affect solubility of compounds. Those values can be employed in estimating the Hildebrand solubility parameters, which account for dispersive forces ($\delta_d$) only, of the materials in the formulation. The method of Hoftyzer and van Krevelen (Properties of polymers: their correlation with chemical structure, their numerical estimation and prediction from additive group contributions. 3rd Edition ed. 1900, Amsterdam: Elsevier. 875) can be used to estimate the Hansen solubility parameter using the values ($\delta_t$) as described in the equation below.

$$\delta_t = \sqrt{\delta_d^2 + \delta_p^2 + \delta_h^2}$$

Compounds with similar values for $\delta$ are likely to be miscible because the energy of mixing from intramolecular interactions is balanced with the energy of mixing from intermolecular interactions. The difference between the solubility parameters ($\Delta\delta$) of two materials gives an estimation of the likelihood that they will be miscible. Greenhalgh et. al. demonstrated that compounds with $\Delta\delta_t < 7$ Mpa$^{1/2}$ were likely to be miscible and compounds with $\Delta\delta_t > 10$ Mpa$^{1/2}$ were likely to be immiscible.

Table shows the calculated solubility parameters for guaifenesin, ketoprofen and polyethylene oxide.

|  | $\delta_d$ | $\delta_p$ | $\delta_h$ | $\delta_t$ |
|---|---|---|---|---|
| Guiafenesin | 20.3 | 0.31 | 18.4 | 27.5 |
| Ketoprofen | 18.7 | 0.18 | 7.5 | 20.2 |
| PEO | 17.8 | 0.56 | 0.1 | 20.0 |

The $\Delta\delta_t$ value for guaifenesin and PEO is 7.5 (GFN–PEO)=7.5 and for ketoprofen and PEO is 0.2 (KTP–PEO). On this basis, one would expect the ketoprofen to be readily soluble in PEO; therefore, PEO would be a suitable polymer for use in a reservoir layer containing ketoprofen. The same type of calculation can be conducted with other polymer and drug or polymer and excipient combinations to facilitate in selection of materials suitable for formulating the reservoir layer.

The solubility parameters can be determined for individual polymers in each layer and, according to the above principles, can be use to develop formulations having the desired properties.

Polymers and polymer blends are selected based upon their predicted likelihood of miscibility. Polymer miscibility promotes adhesion during lamination and coextrusion by polymer chain entanglements between the layers.

In some embodiments, the reservoir layer and the backing layer have PEO as the at least one polymer in common. The PEO can be present as a single grade of polymer or as a combination of two, three or more different grades of polymer. In some embodiments, the reservoir layer has two polymers in common: including Hydroxypropyl cellulose, ethyl cellulose, hydroxypropyl methyl cellulose, gantrez, and others known to one of ordinary skill in the art.

The strength of interlayer adhesion in a laminate will be sufficiently high such that the reservoir layer and the backing layer cannot be pulled apart by hand. Adhesion between the two layers can be measured using an Instron (ASTM Method D882-02). In this technique, grips are applied to each layer, and the force required to cause a rupture is determined.

When the backing layer and reservoir layer do not have a sufficient amount of polymer in common or sufficient miscibility, the strength of interlayer adhesion will be unacceptably low and the layers, in their entirety or significant portions thereof, can be pulled apart by hand.

Generally, the reservoir layer and the backing layer possess melt flow indices that are not too dissimilar if the layers are to be coextruded. This is particularly true when a feedblock die assembly is used. This might not be necessarily required if a dual manifold extrusion die is use to coextrude the layer. For coextrusion, their melt flow indices will generally fall within individual predefined ranges and that those ranges overlap at least to some predefined extent. For example, the melt flow index of the reservoir layer can be within no more than 75% or within no more than 50% of the melt flow index of the backing layer. As used herein, the term melt flow index is taken to mean the amount, in grams, of a resin which can be forced through a plastometer or rheometer (as defined in ASTM D1238) in ten minutes at a given temperature and force.

Generally, the melt flow index of the reservoir layer composition will be within the range of 0.1-80 or at least 0.5 and/or no more than 200 or about 2 to about 20. The melt flow index of the backing layer composition will be within the range of preferably 10:1 or more preferably 5:1 or most preferably 1:1 relative to the reservoir layer. As a result of keeping the melt flow index of the individual layers within a certain percentage of each other, the laminate will possess a uniform transverse cross-section and/or a uniform longitudinal cross-section.

The melt flow index of a layer can be adjusted by increasing or decreasing the amount of one or more materials within a layer. The melt flow index can be decreased by including a higher amount (or a higher relative percentage) of a high viscosity polymer in a layer. A high molecular weight polymer generally possesses a higher viscosity than a low molecular weight polymer; therefore increasing the amount (or relative percentage) of high molecular weight polymer in the layer will increase its melt flow index. For example, increasing the amount of PEO grade 3 in a layer will increase the melt flow index of the layer. Conversely, decreasing the amount (or relative percentage) of higher molecular weight polymer will cause a decrease in the melt flow index of a layer. Likewise, increasing the amount of a dispersed solid in a layer will increase the melt flow index.

Since some polymers have very high viscosity, they are used in combination with a plasticizer to make the polymer hot-melt extrudable. Consequently, the melt flow index of a layer can also be increased by decreasing the amount (or relative percentage) of plasticizer in the layer. Conversely, the melt flow index of a layer can be decreased by increasing the amount (or relative percentage) of plasticizer in the layer.

Figure 15:
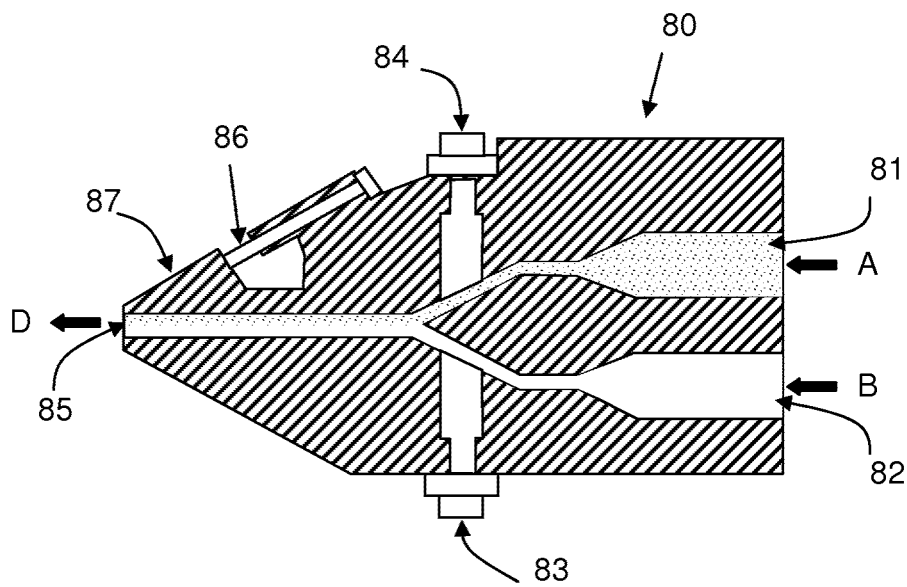
FIG. 15 depicts a partial longitudinal cross-section of a dual manifold extrusion die.

The hot-melt extrusion process of the invention can be conducted with many different types of extrusion dies and assemblies. FIG. 15 depicts a partial cross-sectional view of a dual manifold (multi-manifold) coextrusion film (or sheet) die assembly (80). The assembly comprises two feed ports (81 and 82) by way of which molten feed material (molten drug composition and backing layer composition) are forced into the assembly in the direction of arrows (A and B, respectively). As the molten material traverses the assembly, each composition is individually formed into a molten layer the thickness of which is controlled with respective adjustable chocker bars (83 and 84). While in the molten state, the layers then contact each other in a common conduit in which they are forced together prior to exiting the extrusion assembly via the die orifice (85) in the direction of arrow (D). The adjustment screw (86) serves to control the final thickness of the laminate by controlling the position of the die lip (87). The molten composition in the barrel of the die is depicted as a bi-layered composition, since the manifold received drug composition via port (81) and backing composition via port (82).

Figure 16:
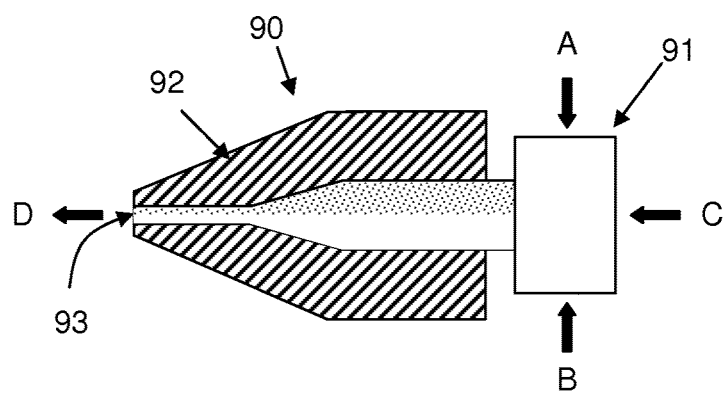
FIG. 16 depicts a partial longitudinal cross-section of a feed block type of extrusion assembly.

FIG. 16 depicts a cross-sectional view of a feedblock type extrusion assembly (90) comprising a feedblock (91) and an extrusion die (92). The feedblock receives molten composition (in the direction of arrows A-C) via two or more ports. While in the molten state and before being shaped by the die, the molten compositions are forced together to form a molten laminate which is then forced through the die to exit via the die orifice (93) in the direction of arrow (D). The molten composition in the barrel of the die is depicted as a bi-layered composition, since the feedblock received drug composition via port A and backing composition via port B.

The laminate of the invention typically possesses a content uniformity, with respect to active agent, sufficiently high to render it suitable for pharmaceutical use. Content uniformity of the laminate is determined by HPLC. A laminate of the invention typically possesses a content uniformity of not less than 100±15% of label claim. The high degree of content uniformity may or may not be dependent upon the unit dose size; however, the invention contemplates that a unit dose of the laminate will be sufficiently large to permit manual manipulation and administration by a subject and sufficiently small to permit transdermal administration to the intended surface of a subject.

Figure 6:
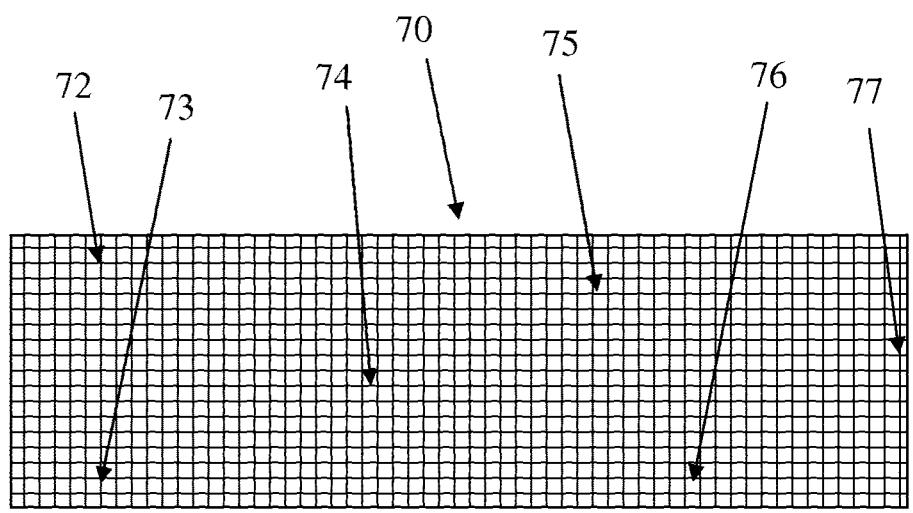
FIG. 6 depicts a top plan view of a laminate divided into individual unit doses.

When a laminate of the invention has a uniform transverse cross-section and/or a uniform longitudinal cross-section, it can be divided into equally-sized unit doses having a high degree of content uniformity. FIG. 6 depicts a sheet-shaped laminate (70) having a uniform transverse cross-section and a uniform longitudinal cross-section. The laminate is cut into equally sized unit doses, as indicated. When the laminate has a uniform transverse cross-section, the dose content of the unit dose (73) will be approximately equal to the dose content of the unit dose (76). When the laminate has a uniform longitudinal cross-section, the dose content of the unit dose (73) will be approximately equal to the dose content of the unit dose (72). When the laminate has a uniform transverse cross-section and a uniform longitudinal cross-section, the dose content of the unit dose (72-77) distributed throughout the laminate will be substantially equal; therefore, the laminate will have a high degree of content uniformity. By "high degree of content uniformity" is meant that the dose of active agent in individual unit doses obtained from the same laminate will not vary more than ±15% of the average amount of active agent present per unit dose.

A unit dose can be cut into a predetermined form with dimensions that provide an effective dose being delivered, good adhesion and comfort during delivery. In some embodiments, the unit dose has an average and exposed surface area between 32 and 250 mm$^2$, such as 32-137 (or 30-140) mm$^2$ for 5 mg doses, 40-55 mm$^2$ for 7.5 mg doses, 130-145 mm$^2$ for 10 mg doses, 99-121 (or 95 to 125) mm$^2$ for 12.5 mg doses, 91-142 (or 90-145) mm$^2$ for 15 mg doses and 107-241 (or 105-245) mm$^2$ for 20 mg doses. In other embodiments, the unit dose has a surface area to dose ratio of 5 to 35 mm$^2$/mg testosterone based upon the exposed reservoir surface, such as 6-33 (or 5 to 35) mm$^2$/mg for 5 mg doses, 6-8 (or 5-10) mm$^2$/mg for 7.5 mg doses, 13-15 (or 10-15) mm$^2$/mg for 10 mg doses, 8-10 (or 5-10) mm$^2$/mg for 12.5 mg doses, 6-10 (or 5-10) mm$^2$/mg for 15 mg doses, and 7-12 (or 5-15) mm$^2$/mg for 20 mg doses.

In some embodiments of the laminate, the unit dose provides a circadian rhythm type of plasma profile for the active agent(s) included within the laminate. Circadian rhythm type plasma profile is defined as a unit dose that provides a substantially similar release profile over each 24-hour period. In some embodiments, the circadian rhythm profile is characterized by two phases, an elevated phase wherein the plasma concentration of active agent is maintained at or above a predetermined plasma concentration and a reduced phase wherein the plasma concentration of active agent is maintained at or below a predetermined plasma concentration. For example, the laminate can provide a biphasic plasma profile having a first elevated phase at or above a predetermined plasma concentration of active for a predetermined period following administration to a subject and a subsequent reduced phase at or below a predetermined plasma concentration of active for a predetermined period following administration to a subject. In exemplary embodiments, the elevated phase can be maintained for between about 8 and 15 hours, such as about 12 hours, wherein the remainder of the release profile, about 16 to 9 hours respectively, is maintained in the reduced phase in a 24-hour period.

For example, a unit dose comprising testosterone can provide a biphasic plasma profile having a first elevated phase above 500 ng/dL for the period of 0.5 to 4 hours after administration and a subsequent reduced phase of 500 ng/dL or below for a period of 20 to 23.5 hours, respectively, after administration in a 24-hour period. Such a laminate can be suitable for up to 6 times daily administration. In some embodiments, the laminate provides a biphasic plasma profile having a first elevated phase above 500 ng/dL for the period of 0.5 to 12 hours after administration and a subsequent reduced phase of 500 ng/dL or below for the period of 12 to 23.5 hours, respectively, after administration in a 24-hour period. Such a laminate can be suitable for up to twice daily administration. In some embodiments, the laminate provides a biphasic plasma profile having a first elevated phase above 500 ng/dL for the period of 1 to 15 hours after administration and a subsequent reduced phase of 500 ng/dL or below for the period of 9 to 23 hours, respectively, after administration in a 24-hour period. Such a laminate can be suitable for up to twice daily administration. In some embodiments, the laminate provides a biphasic plasma profile having a first elevated phase above 500 ng/dL for the period of 2 to 12 hours after administration and a subsequent reduced phase of 500 ng/dL or below for the period of 12 to 22 hours, respectively, after administration in a 24-hour period. Such a laminate can be suitable for up to twice daily administration. In some embodiments, the laminate provides a biphasic plasma profile having a first elevated phase above 500 ng/dL for the period of 1 to 15 hours after administration and a subsequent reduced phase of 500 ng/dL or below for the period of 9 to 23 hours, respectively, after administration in a 24-hour period. Such a laminate can be suitable for up to twice daily administration. In some embodiments, the laminate provides a biphasic plasma profile having a first elevated phase above 350 ng/dL for the period of 0.5 to 12 hours after administration and a subsequent reduced phase of 350 ng/dL or below for the period of 12 to 23.5 hours, respectively, after administration in a 24-hour period. Such a laminate can be suitable for up to twice daily administration.

Exemplary embodiments include those wherein a unit dose of the laminate provides a blood plasma concentration of testosterone in the range of about 300-1000 ng/dl for a period of at least 6 hours, such as at least 8 hours or at least 12 hours after mucosal buccal application to a subject. In some embodiments, the unit dose of the film provides a blood plasma concentration of testosterone in the range of about 300-1000 ng/dl for a period of about 30 hours, such as about 24 hours after mucosal buccal application to a subject. The unit dose of film can be administered once daily and is maintained in contact with the buccal mucosa for at least 6 hours, such as at least 8 hours or at least 12 hours or for 24 hours. Some embodiments of the invention include a unit dose that provides an in vivo monomodal or bimodal testosterone plasma concentration profile following transdermal administration.

In some embodiments, a unit dose of the laminate can comprises 0.1 to 20 mg of testosterone, such as between 1 and 30% by weight of the reservoir layer, such as between 10 and 20% by weight (e.g. about 15% by weight).

When a release liner layer is present, it temporarily adheres to the bioadhesive layer during storage of the HME composition, and it is removable by hand before administration of the HME composition to a subject. The release layer may or may not be coextruded with the other two layers. The release liner layer is removably affixed to the reservoir layer and/or backing layer. Any release liner layer that can temporarily adhere to the reservoir layer will be suitable for use according to the invention. Exemplary non-limiting suitable release layers obtainable from commercial sources include DOW SARANEX™, BLF, 3M CoTran and SCOTCHPAK, Delstar Stratex and Delnet.

The release layer is attached to the face of the reservoir layer that is opposite the backing layer such that the release layer and backing layer oppose one another. In other words, the reservoir layer is between the release layer and the backing layer. The contact surface area of the release layer can be the same size as or bigger than the corresponding contact surface of the reservoir layer.

The laminate may also contain various functional excipients, such as: hydrophilic polymer, antioxidant, super-disintegrant, surfactant including amphiphillic molecules, wetting agent, stabilizing agent, retardant, thermal lubricant, colorant, solubilizer, chelating agent, similar functional excipient, or combination thereof, and plasticizers including citrate esters, polyethylene glycols, PG, triacetin, diethylphthalate, castor oil, and others known to those or ordinary skill in the art. The laminate may also include an acidifying agent, adsorbent, alkalizing agent, buffering agent, colorant, flavorant, sweetening agent, diluent, opaquant, complexing agent, fragrance, preservative or a combination thereof.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

A buffering agent is used to resist change in pH upon dilution or addition of acid or alkali. Such compounds include, by way of example and without limitation, potassium metaphosphate, potassium phosphate, monobasic sodium acetate and sodium citrate anhydrous and dihydrate, salts of inorganic or organic acids, salts of inorganic or organic bases, and others known to those of ordinary skill in the art.

As used herein, the term "alkalizing agent" is intended to mean a compound used to provide alkaline medium for product stability. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art.

As used herein, the term "colorant" is intended to mean a compound used to impart color to solid (e.g., tablets) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red, other F.D. & C. dyes and natural coloring agents such as grape skin extract, beet red powder, beta-carotene, annato, carmine, turmeric, paprika, and other materials known to one of ordinary skill in the art. The amount of coloring agent used will vary as desired.

Exemplary chelating agents include EDTA, polycarboxylic acids, polyamines, derivatives thereof, and others known to those of ordinary skill in the art.

Exemplary hydrophilic polymers which can be a primary or secondary polymeric carrier that can be included in the composition include poly(vinyl alcohol) (PVA), polyethylene-polypropylene glycol (e.g. poloxamer), carbomer, polycarbophil, or chitosan. The "hydrophilic polymers" of the present invention include one or more of hydroxypropyl methylcellulose, carboxymethylcellulose, hydroxypropyl cellulose, hydroxyethyl cellulose, methylcellulose, natural gums such as gum guar, gum acacia, gum tragacanth, or gum xanthan and povidone. "Hydrophilic polymers" also include polyethylene oxide, sodium carboxymethycellulose, hydroxyethyl methyl cellulose, hydroxymethyl cellulose, carboxypolymethylene, polyethylene glycol, alginic acid, gelatin, polyvinyl alcohol, polyvinylpyrrolidones, polyacrylamides, polymethacrylamides, polyphosphazines, polyoxazolidines, poly(hydroxyalkylcarboxylic acids), carrageenate alginates, carbomer, ammonium alginate, sodium alginate, or mixtures thereof.

Exemplary hydrophobic polymers include alkylcelluloses, ethyl cellulose, Eudragit RS, waxes, polyesters, combinations thereof, and others known to those of ordinary skill in the art.

Thermal lubricants include glyceryl monosterarate, vitamin E succinate, glycerol monooleate, combinations thereof, and others known to those of ordinary skill in the art.

Solubilizers include cyclodextrins, povidone, combinations thereof, and others known to those of ordinary skill in the art.

As used herein, the term "antioxidant" is intended to mean an agent that inhibits oxidation and thus is used to prevent the deterioration of preparations by oxidation due to the presence of oxygen free radicals or free metals in the composition. Such compounds include, by way of example and without limitation, ascorbic acid, ascorbyl palmitate, butylated hydroxyanisole, butylated hydroxytoluene (BHT), hypophosphorous acid, monothioglycerol, sodium ascorbate, sodium formaldehyde sulfoxylate and sodium metabisulfite and others known to those of ordinary skill in the art. Other suitable antioxidants include, for example, vitamin C, BHT, BHA, sodium bisulfite, vitamin E and its derivatives, propyl gallate or a sulfite derivative.

As used herein, the term "disintegrant" is intended to mean a compound used in solid dosage forms to promote the disruption of a solid mass (layer) into smaller particles that are more readily dispersed or dissolved. Exemplary disintegrants include, by way of example and without limitation, starches such as corn starch, potato starch, pre-gelatinized and modified starches thereof, sweeteners, clays, bentonite, microcrystalline cellulose (e.g., Avicel™), carboxymethylcellulose calcium, croscarmellose sodium, alginic acid, sodium alginate, cellulose polyacrilin potassium (e.g., Amberlite™), alginates, sodium starch glycolate, gums, agar, guar, locust bean, karaya, pectin, tragacanth, crospovidone and other materials known to one of ordinary skill in the art. A superdisintegrant is a rapidly acting disintegrant. Exemplary superdisintegrants include crospovidone and low substituted HPC.

Suitable surfactants include Polysorbate 80, sorbitan monooleate, sodium lauryl sulfate or others. Soaps and synthetic detergents may be employed as surfactants. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly(oxyethylene)-block-poly(oxypropylene) copolymers; and amphoteric detergents, for example, alkyl β-aminopropionates and 2-alkylimidazoline quaternary ammonium salts; and mixtures thereof.

Wetting agent is an agent that decreases the surface tension of a liquid. Wetting agents would include alcohols, glycerin, proteins, peptides water miscible solvents such as glycols, hydrophilic polymers Polysorbate 80, sorbitan monooleate, sodium lauryl sulfate, fatty acid alkali metal, ammonium, and triethanolamine salts, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly(oxyethylene)-block-poly(oxypropylene) copolymers; and amphoteric detergents, for example, alkyl β-aminopropionates and 2-alkylimidazoline quaternary ammonium salts; and mixtures thereof.

Retardants are agents that are insoluble or slightly soluble polymers with a Tg above 45° C., or above 50° C. before being plasticized by other agents in the formulation including other polymers and other excipients needed for processing. The excipients include waxes, acrylics, cellulosics, lipids, proteins, glycols, and the like.

A desiccant can be used to aid in storing a formulation according to the invention. Suitable desiccants include sodium sulfate, calcium sulfate, magnesium sulfate, sodium hydroxide, sodium bicarbonate, clay, vermiculite, paper, activated alumina, zeolite, calcium chloride, molecular sieve, or anhydrous chemicals. In some cases a desiccant is needed if the matrix materials or the drug are hygroscopic since moisture may affect the stability of the HME composition and/or drug therein.

As used herein, the term "opaquant" is intended to mean a compound used to render a composition opaque. May be used alone or in combination with a colorant. Such compounds include, by way of example and without limitation, titanium dioxide and other materials known to one of ordinary skill in the art.

Some of the materials listed herein may be too brittle or may have Tg values that are generally too high rendering them too difficult to extrude. The glass transition temperature is reduced upon the addition of a plasticizer. As used herein, the glass transition temperature is taken to mean the temperature at which a solid material softens or melts (or the glass transition temperature (Tg) is the temperature at which a polymer changes during the heat cycle from a brittle substance (glass) to a rubbery mass). Such materials can be combined with one or more plasticizers to render them thermoformable. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the film of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutyl sebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers may be used in the present formulation. The PEG based plasticizers are available commercially or can be made by a variety of methods, such as disclosed in *Poly(ethylene glycol) Chemistry: Biotechnical and Biomedical Applications* (J. M. Harris, Ed.; Plenum Press, NY) the disclosure of which is hereby incorporated by reference.

Preservatives include compounds used to prevent the growth of microorganisms. Suitable preservatives include, by way of example and without limitation, benzalkonium chloride, benzethonium chloride, benzyl alcohol, cetylpyridinium chloride, chlorobutanol, phenol, phenylethyl alcohol, phenylmercuric nitrate and thimerosal and others known to those of ordinary skill in the art.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors that have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particular flavors are the grape and cherry flavors and citrus flavors such as orange.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

The hot-melt extruded composition of the invention will include at least an effective amount of testosterone. By the term "effective amount", it is understood that, with respect to, for example, pharmaceuticals, a therapeutically effective amount is contemplated. A therapeutically effective amount is the amount or quantity of drug that is sufficient to elicit the required or desired therapeutic response, or in other words, the amount that is sufficient to elicit an appreciable biological response when administered to a patient.

Where possible, any of the materials employed herein can be present in its free acid, free base or pharmaceutically acceptable salt form. As used herein, "pharmaceutically acceptable salts" refer to derivatives of the disclosed compounds wherein the compound is modified by making acid or base salts thereof. Examples of pharmaceutically acceptable salts include, but are not limited to, mineral or organic acid salts of the drug. The pharmaceutically acceptable salts include the conventional non-toxic salts, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and other known to those of ordinary skill in the pharmaceutical sciences. Lists of suitable salts are found in texts such as *Remington's Pharmaceutical Sciences*, 18th Ed. (Alfonso R. Gennaro, ed.; Mack Publishing Company, Easton, Pa., 1990); *Remington: the Science and Practice of Pharmacy* 19$^{th}$ Ed. (Lippincott, Williams & Wilkins, 1995); *Handbook of Pharmaceutical Excipients*, 3$^{rd}$ Ed. (Arthur H. Kibbe, ed.; Amer. Pharmaceutical Assoc., 1999); the *Pharmaceutical Codex Principles and Practice of Pharmaceutics* 12$^{th}$ Ed. (Walter Lund ed.; Pharmaceutical Press, London, 1994); The United States Pharmacopeia: The National Formulary (United States Pharmacopeial Convention); and *Goodman and Gilman's: the Pharmacological Basis of Therapeutics* (Louis S. Goodman and Lee E. Limbird, eds.; McGraw Hill, 1992), the disclosures of which are hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term testosterone means all available forms of the compound including crystalline, semi-crystalline, amorphous, hydrate, anhydrous, diastereomeric, and enantiomeric forms. The term "testosterone" also includes derivatives thereof, such as the C17-esters thereof. Testosterone (17β-hydroxyandrost-4-en-3-one) is commercially available from several commercial sources including: Pharmacia & Upjohn (Kalamazoo, Mich., 49001); and Diosynth B.V. (a Division of Akzo Nobel) (The Netherlands).

Testosterone and any other materials included in the laminate can be present in any particle size suitable for hot-melt extrusion. Fine particle sizes and larger particle sizes can be used. It can be added as a liquid, solid, emulsion, or any other suitable form. Prior to inclusion in the reservoir layer, the testosterone API can have an average particle size of less than 250µ and, upon inclusion, the testosterone can be homogeneously dispersed throughout the reservoir layer. Homogeneously dispersed is defined to mean distributed and mixed uniformly in structure or composition throughout the matrix.

There are several methods well known in the pharmaceutical literature for producing fine drug particles in the micro or nanometer size range. These methods can be divided into three primary categories: (1) mechanical micronization (2) solution based phase separation and (3) rapid freezing techniques. Drug particles made according to any of these techniques will be suitable for use in the present pharmaceutical composition.

Such processes include mechanical milling by ball mill, jet mill, or other similar grinding process; solution based phase separation techniques such as spray drying, emulsification/evaporation, emulsification/solvent extraction, complex coacervation, gas antisolvent precipitation (GAS), precipitation with a compressed antisolvent (PCA), aerosol solvent extraction system (ASES), evaporative precipitation into aqueous solution (EPAS), supercritical antisolvent (SAS), solution-enhanced dispersion by supercritical fluids (SEDS), rapid expansion from supercritical to aqueous solutions (RESAS), pressure induced phase separation (PIPS); or freezing techniques such as spray freezing into liquid (SFL) and ultra rapid freezing (URF). Detailed descriptions of these methods are included in references cited herein, the entire disclosures of which are hereby incorporated by reference.

Mechanical micronization is most commonly done by milling techniques that can produce particles in the range of 1 to 20 microns. The most common processes utilized for this type of mechanical particle size reduction are ball and jet milling.

There are many solution based phase separation processes documented in the pharmaceutical literature for producing micro and nano-sized drug particles. Some of the more commonly known processes are spray drying, emulsification/evaporation, emulsification/solvent extraction, and complex coacervation. Some of the lesser-known processes are, for the sake of brevity, listed below along with their respective illustrating references: a) gas antisolvent precipitation (GAS)—WO9003782, EP0437451, DK59091; b) precipitation with a compressed antisolvent (PCA)—U.S. Pat. No. 5,874,029; c) aerosol solvent extraction system (ASES); d) evaporative precipitation into aqueous solution (EPAS)—US patent application 20040067251; e) supercritical antisolvent (SAS); f) solution—enhanced dispersion by supercritical fluids (SEDS); and g) rapid expansion from supercritical to aqueous solutions (RESAS).

Freezing techniques for producing micro or nano-sized drug particles are listed below along with their respective illustrating references: a) spray freezing into liquid (SFL)—WO02060411, USPTO App. No. 2003054042, and No. 2003024424; and b) ultra rapid freezing (URF).

Drug-containing particles may or may not undergo substantial aggregation or agglomeration during hot-melt extrusion and/or will be disaggregated to essentially primary particles during hot-melt extrusion due to the intense mixing and agitation that occurs during the process. In some cases, the extrudate may need to be processed more than one time through the extruder in order to provide the desired degree of disaggregation. As used herein, the term "disaggregate", as used in reference to the drug-containing particles, means to reduce a loosely bound agglomerate to essentially its primary constituent particles. As used herein, the term "to agglomerate" or "agglomeration", as used in reference to the drug-containing particles means individual particles form a larger particle.

As used herein, the terms "therapeutic compound", "therapeutic agent", "active agent" and "drug" are used interchangeably, unless otherwise specified. The process of the invention can be used to prepare composition and dosage forms comprising essentially any one or more active agents. Active agents include physiological substances or pharmacological active substances that produce a systemic or localized effect or effects on animals and human beings.

Active agents include pesticides, herbicides, insecticides, antioxidants, plant growth instigators, sterilization agents, catalysts, chemical reagents, food products, nutrients, cosmetics, vitamins, minerals, dietary supplements, sterility inhibitors, fertility instigators, microorganisms, flavoring agents, sweeteners, cleansing agents and other such compounds for pharmaceutical, veterinary, horticultural, household, food, culinary, agricultural, cosmetic, industrial, cleansing, confectionery and flavoring applications. The active agent can be present in its neutral, ionic, salt, basic, acidic, natural, synthetic, diastereomeric, isomeric, enantiomerically pure, racemic, hydrate, chelate, derivative, analog, or other common form.

The laminate of the invention can include one or more other drugs known to be useful for coadministration with testosterone. Representative steroidal drugs are prednisone, prednisolone, cortisone, cortisol and triamcinolone; androgenic steroids such as methyltesterone, testosterone, and fluoxmesterone; estrogenic steroids such as 17β-estradiol, α-estradiol, estriol, α-estradiol 3 benzoate, and 17-ethynylestradiol-3-methyl ether; progestational steriods such as progesterone, 19-nor-pregn-4-ene-3,20-dione, 17-hydroxy-19-nor-17-α-pregn-5(10)-ene-20-yn-3-one, 17α-ethynyl-17-hydroxy-5(10)-estren-3-one, and 9β, 10α-pregna-4,6-diene-3,20-dione.

Representative estrogen antagonist-agonist drugs are clomiphene citrate and raloxifene HCl.

Further therapeutic compounds which can be formulated into the present composition also include antibacterial substance, antihistamine (histamine receptor inhibitor), decongestant, anti-inflammatory agent, antiparasitic agent, antiviral agent, local anesthetic, antifungal agent, amoebicidal agent, trichomonocidal agent, analgesic agent, antiarthritic agent, antiasthmatic agent, anticoagulant agent, anticonvulsant agent, antidepressant agent, antidiabetic agent, antineoplastic agent, antipsychotic agent, neuroleptic agent, antihypertensive agent, muscle relaxant, depressant agent, hypnotic agent, sedative agent, psychic energizer, tranquilizer, antiparkison agent, muscle contractant, anti-microbial agent, antimalarial agent, hormonal agent, contraceptive agent, sympathomimetic agent, diuretic agent, hypoglycemic agent, ophthalmic agent, anti-hypercholesterolemia agent, anti-hypocholesterolemia agent, electrolyte, diagnostic agent, cardiovascular drug, vitamin, nutrient, other type of therapeutic compound known to those of ordinary skill in the pharmaceutical sciences, and combinations thereof.

Representative therapeutic compounds include nutrients and nutritional agents, hematological agents, endocrine and metabolic agents, cardiovascular agents, renal and genitourinary agents, respiratory agents, central nervous system agents, gastrointestinal agents, anti-infective agents, biologic and immunological agents, dermatological agents, ophthalmic agents, antineoplastic agents, and diagnostic agents. Exemplary nutrients and nutritional agents include as minerals, trace elements, amino acids, lipotropic agents, enzymes and chelating agents. Exemplary hematological agents include hematopoietic agents, antiplatelet agents, anticoagulants, coumarin and indandione derivatives, coagulants, thrombolytic agents, antisickling agents, hemorrheologic agents, antihemophilic agents, hemostatics, plasma expanders and hemin. Exemplary endocrine and metabolic agents include sex hormones, uterine-active agents, bisphosphonates, antidiabetic agents, glucose elevating agents, adrenocortical steroids, parathyroid hormone, thyroid drugs, growth hormones, posterior pituitary hormones, octreotide acetate, imiglucerase, calcitonin-salmon, sodium phenylbutyrate, betaine anhydrous, cysteamine bitartrate, sodium benzoate and sodium phenylacetate, bromocriptine mesylate, cabergoline, agents for gout, and antidotes.

Exemplary cardiovascular agents include nootropic agents, antiarrhythmic agents, calcium channel blocking agents, vasodilators, antiadrenergics/sympatholytics, renin angiotensin system antagonists, antihypertensive combinations, agents for pheochromocytoma, agents for hypertensive emergencies, antihyperlipidemic agents, antihyperlipidemic combination products, vasopressors used in shock, potassium removing resins, edetate disodium, cardioplegic solutions, agents for patent ductus arteriosus, and sclerosing agents. Exemplary renal and genitourinary agents include interstitial cystitis agents, cellulose sodium phosphate, anti-impotence agents, acetohydroxamic acid (aha), genitourinary irrigants, cystine-depleting agents, urinary alkalinizers, urinary acidifiers, anticholinergics, urinary cholinergics, polymeric phosphate binders, vaginal preparations, and diuretics. Exemplary respiratory agents include bronchodilators, leukotriene receptor antagonists, leukotriene formation inhibitors, nasal decongestants, respiratory enzymes, lung surfactants, antihistamines, nonnarcotic antitussives, and expectorants. Exemplary central nervous system agents include CNS stimulants, narcotic agonist analgesics, narcotic agonist-antagonist analgesics, central analgesics, acetaminophen, salicylates, nonnarcotic analgesics, nonsteroidal anti-inflammatory agents, agents for migraine, antiemetic/antivertigo agents, antianxiety agents, antidepressants, antipsychotic agents, cholinesterase inhibitors, nonbarbiturate sedatives and hypnotics, nonprescription sleep aids, barbiturate sedatives and hypnotics, general anesthetics, anticonvulsants, muscle relaxants, antiparkinson agents, adenosine phosphate, cholinergic muscle stimulants, disulfuram, smoking deterrents, riluzole, hyaluronic acid derivatives, and botulinum toxins. Exemplary gastrointestinal agents including *H. pylori* agents, histamine H2 antagonists, proton pump inhibitors, sucralfate, prostaglandins, antacids, gastrointestinal anticholinergics/antispasmodics, mesalamine, olsalazine sodium, balsalazide disodium, sulfasalazine, celecoxib, infliximab, esomeprazole, famotidine, lansoprazole, omeprazole, pantoprazole, rabeprazole, tegaserod maleate, laxatives, antidiarrheals, antiflatulents, lipase inhibitors, GI stimulants, digestive enzymes, gastric acidifiers, hydrocholeretics, gallstone solubilizing agents, mouth and throat products, systemic deodorizers, and anorectal preparations. Exemplary anti-infective agents including penicillins, such as amoxicilin, cephalosporins and related antibiotics, carbapenem, monobactams, chloramphenicol, quinolones, fluoroquinolones, tetracyclines, macrolides, such as azithromycin, clarithromycin, and the like, spectinomycin, streptogramins, vancomycin, oxalodinones, lincosamides, oral and parenteral aminoglycosides, colistimethate sodium, polymyxin B sulfate, bacitracin, metronidazole, sulfonamides, nitrofurans, methenamines, folate antagonists, antifungal agents, such as fluconazole, voriconazole, and the like, antimalarial preparations, antituberculosis agents, amebicides, antiviral agents, antiretroviral agents, leprostatics, antiprotozoals, anthelmintics, and CDC anti-infective agents. Exemplary biologic and immunological agents including immune globulins, monoclonal antibody agents, antivenins, agents for active immunization, allergenic extracts, immunologic agents, and antirheumatic agents. Exemplary antineoplastic agents include alkylating agents, antimetabolites, antimitotic agents, epipodophyllotoxins, antibiotics, hormones, enzymes, radiopharmaceuticals, platinum coordination complex, anthracenedione, substituted ureas, methylhydrazine derivatives, imidazotetrazine derivatives, cytoprotective agents, DNA topoisomerase inhibitors, biological response modifiers, retinoids, rexinoids, monoclonal antibodies, protein-tyrosine kinase inhibitors, porfimer sodium, mitotane (o, p'-ddd), and arsenic trioxide. Exemplary diagnostic agents include in vivo diagnostic aids, in vivo diagnostic biologicals, and radiopaque agents.

Representative antibacterial substances are beta-lactam antibiotics, tetracyclines, chloramphenicol, neomycin, gramicidin, bacitracin, sulfonamides, aminoglycoside antibiotics, tobramycin, nitrofurazone, nalidixic acid, penicillin, tetracycline, oxytetracycline, chlorotetracycline, erythromycin, cephalosporins and analogs and the antimicrobial combination of fludalanine/pentizidone. Other representative antibacterial agents include of the poorly water-soluble pyrridone-carboxylic acid type such as benofloxacin, nalidixic acid, enoxacin, ofloxacin, amifloxacin, flumequine, tosfloxacin, piromidic acid, pipemidic acid, miloxacin, oxolinic acid, cinoxacin, norfloxacin, ciprofloxacin, pefloxacin, lomefloxacin, enrofloxacin, danofloxacin, binfloxacin, sarafloxacin, ibafloxacin, difloxacin and salts thereof.

Representative antiparasitic compounds are ivermectin, bephenium, hydroxynaphthoate, praziquantel, nifurtimox, benznidasol, dichlorophen and dapsone. Representative antimalarial compounds are 4-aminoquinolines, 8-aminoquinolines and pyrimethamine.

Representative antiviral compounds are protease inhibitors, neuramidinase inhibitors, commercially available compounds, acyclovir and interferon.

Representative anti-inflammatory drugs include specific or selective COX-2 receptor inhibitors, rofecoxib, celecoxib, etodolac, flurbiprofen, ibuprofen, ketoprofen, ketorolac, nabumetone, piroxicam, suprofen, tolmetin, zileuton, steroids, cyclooxygenase inhibitors, cortisone, hydrocortisone, betamethasone, dexamethasone, fluocortolone, prednisolone, phenylbutazone, triamcinolone, sulindac, indomethacin, salicylamide, naproxen, colchicine, fenoprofen, diclofenac, indoprofen, dexamethasone, allopurinol, oxyphenbutazone, probenecid and sodium salicylamide.

Representative analgesic drugs are diflunisal, aspirin, ibuprofen, profen-type compounds, morphine, codeine, levorphanol, hydromorphone, oxymorphone, oxycodone, hydrocodone, naloxene, levallorphan, etorphine, fentanyl, bremazocine, meperidine, nalorphine, tramadol, and acetaminophen.

Representative antihistamines and decongestants are acrivastine, astemizole, norastemizol, brompheniramine, cetirizine, clemastine, diphenhydramine, ebastine, famotidine, fexofenadine, meclizine, nizatidine, perilamine, promethazine, ranitidine, terfenadine, chlorpheniramine, cimetidine, tetrahydrozoline, tripolidine, loratadine, desloratadine, antazoline, and pseudoephedrine.

Representative antiasthma drugs are theophylline, ephedrine, beclomethasone dipropionate and epinephrine.

Representative anticoagulants are heparin, bishydroxycoumarin, and warfarin.

Representative psychic energizers are isocoboxazid, nialamide, phenelzine, imipramine, tranycypromine, and parglyene.

Representative anticonvulsants are clonazepam, phenobarbital, mephobarbital, primidone, enitabas, diphenylhydantion, ethltion, pheneturide, ethosuximide, diazepam, phenyloin carbamazepine, lamotrigine, lorazepam, levetiracetam, oxcarbazepine, topiramate, valproic acid, chlorazepate, gabapentin, felbamate, tiagabine and zonisamide.

Representative antidepressants are amitriptyline, chlordiazepoxide perphenazine, protriptyline, imipramine, doxepin, venlafaxine, o-desmethyl venlafaxine, citalopram, escitalopram, bupropion, clomipramine, desipramine, nefazodone, fluoxetine, fluvoxamine, maprotiline, mirtazapine, nortriptyline, paroxetine, phenelzine, tranylcypromine, sertraline, trazodone, trimipramine, and amoxapine.

Representative antidiabetics are sulphonylureas, such as tolbutamide, chlorpropamide, tolazamide, acetohexamide, glibenclamide, gliclazide, 1-butyl-3-metanilylurea, carbutamide, glibonuride, glipizide, glyburide, gliquidone, glisoxepid, glybuthiazole, glibuzole, glyhexamide, glymidine, glypinamide, phenbutamide, and tolcyclamide; thiazolidinediones (glitazones), such as rosiglitazone, pioglitazone, and troglitazone; biguanidines, such as metformin; and other antidiabetic agents, such as nateglinide, repaglinide, insulin, somatostatin and its analogs, chlorpropamide, isophane insulin, protamine zinc insulin suspension, globin zinc insulin, and extended insulin zinc suspension.

Representative antineoplastics are chlorambucil, cyclophosphamide, triethylenemelamine, thiotepa, hexamethylmelamine, busulfan, carmustine, lomustine, dacarbazine, arabinoside cytosine, mercaptopurine, azathiprine, vincristine, vinblastine, taxol, etoposide, actinomycin D, daunorubicin, doxorubicin, bleomycin, mitomycin; cisplatin; hydroxyurea, procarbazine, aminoglutethimide, tamoxifen, adriamycin, fluorouracil, methotrexate, mechlorethamine, uracil mustard, 5-fluorouracil, 6-6-thioguanine and procarbazine asparaginase.

Representative steroidal drugs are prednisone, prednisolone, cortisone, cortisol and triamcinolone; androgenic steroids such as methyltesterone, testosterone, and fluoxmesterone; estrogenic steroids such as 17β-estradiol, α-estradiol, estriol, α-estradiol 3 benzoate, and 17-ethynylestradiol-3-methyl ether; progestational steriods such as progesterone, 19-nor-pregn-4-ene-3,20-dione, 17-hydroxy-19-nor-17-α-pregn-5(10)-ene-20-yn-3-one, 17α-ethynyl-17-hydroxy-5(10)-estren-3-one, and 9β, 10α-pregna-4,6-diene-3,20-dione.

Representative estrogen antagonist-agonist drugs are clomiphene citrate and raloxifene HCl.

Representative antipsychotics are prochlorperazine, lithium carbonate, lithium citrate, thioridazine, molindone, fluphenazine, trifluoperazine, perphenazine, amitriptyline, trifluopromazine, chlorpromazine, clozapine, haloperidol, loxapine, mesoridazine, olanzapine, quetiapine, ziprasidone, risperidone, pimozide, mesoridazine besylate, chlorprothixene, and thiothixene.

Representative hypnotics and sedatives are pentobarbital sodium, phenobarbital, secobarbital, thiopental, heterocyclic hypnotics, dioxopiperidines, imidazopyridines, such as zolpidem tartrate, glutarimides, diethylisovaleramide, α-bromoisovaleryl urea, urethanes, disulfanes.

Representative antihypertensives are nifedipine, verapamil, diltiazem, felodipine, amlodipine, isradipine, nicardipine, nisoldipine, nimodipine, bepridil, enalapril, captopril, lisinopril, benazepril, enalaprilat, espirapril, fosinopril, moexipril, quinapril, ramipril, perindopril, trandolapril, furosemide, bumetanide, ethacrynic acid, torsemide, muzolimide, azosemide, piretanide, tripamide, hydrochlorothiazide, chlorthalidone, indapamide, metozalone, cyclopenthiazide, xipamide, mefruside, dorzolamide, acetazolamide, methazolamide, ethoxzolamide, cyclothiazide, clopamide, dichlorphenamide, hydroflumethiazide, trichlormethiazide, polythiazide, benzothiazide, spironolactone, methyldopa, hydralazine, clonidine, chlorothiazide, deserpidine, timolol, propranolol, metoprolol, pindolol, acebutolol, prazosin hydrochloride, methyl dopa (L-β-3,4-dihydroxyphenylalanine), pivaloyloxyethyl ester of α-methyldopa hydrochloride dihydrate, candesartan cilexetil, eprosartan mesylate, losartan potassium, olmersartan medoxomil, telmisartan, valsartan, and reserpine.

Representative anti-incontinence agents include oxybutynin, darifenacin, and tolterodine.

Representative tranquilizers are chloropromazine, promazine, fluphenazine, reserpine, deserpidine, meprobamate, and benezodiazepines (anxyiolitic, sedatives, and hypnotics) such as alprazolam, chlordiazepoxide, diazepam, lorazepam, oxazepam, temazepam, and triazolam.

Representative anti-spasmodics and muscle contractants are atropine, scopolamine, methscopolamine, oxyphenonium, papaverine, and prostaglandins such as $PGE_1$ $PGE_2$ $PGF_{1\alpha}$ $PGF_{2\alpha}$ and PGA.

Representative local anesthetics are benzocaine, procaine, lidocaine, maepaine, piperocaine, tetracaine and dibucaine.

Representative muscle relaxants are alcuronium, alosetron, aminophylline, baclofen, carisoprodol, chlorphenesin, chlorphenesin carbamate, chlorzoxazone, chlormezanone, dantrolene, decamethonium, dyphylline, eperisione, ethaverine, gallamine triethiodide, hexafluorenium, metaxalone, metocurine iodide, orphenadrine, pancuronium, papaverine, pipecuronium, theophylline, tizanidine, tolperisone, tubocurarine, vecuronium, idrocilamide, ligustilide, cnidilide, senkyunolide, succinylcholine-chloride, danbrolene, cyclobenzaprine, methocarbamol, diazepam, mephenesin, methocarbomal, trihexylphenidyl, pridinol (pridinolum), and biperiden.

Representative anti-Parkinson agents are carbidopa, levodopa, ropinirole, pergolide mesylate, rasagiline, pramipexole, entacapone, benzacide, bromocriptine, selegiline, amantadine, trihexylphenidyl, biperiden, pridinol mesylate, and tolcapone.

Representative anti-Dementia and anti-Alzheimer disease agents are memantine, donepexil, galantamine, rivastigmine, and tacrine Representative sympathomimetic drugs are albuterol, epinephrine, amphetamine ephedrine and norepinephrine.

Representative cardiovascular drugs are procainamide, procainamide hydrochloride, amyl nitrite, nitroglycerin, dipyredamole, sodium nitrate and mannitol nitrate.

Representative diuretics are chlorothiazide, acetazolamide, methazolamide, triamterene, furosemide, indapamide, and flumethiazide.

Representative β-blockers are caravedilol, pindolol, propranolol, practolol, metoprolol, esmolol, oxprenolol, timolol, atenolol, alprenolol, and acebutolol.

Representative phosphodiesterase inhibitors are vardenafil HCl and sildenafil citrate.

Representative antilipemic agents are atorvastatin, cerivastatin, clofibrate, fluvastatin, gemfibrozil, lovastatin, mevinolinic acid, niacin, pravastatin, and simvastatin.

Representative antigout drugs are colchicine, allopurinol, probenecid, sulfinpyrazone, and benzbromadone.

Representative nutritional agents are ascorbic acid, niacin, nicotinamide, folic acid, choline biotin, panthothenic acid, and vitamin $B_{12}$, essential amino acids; essential fats.

Representative electrolytes are calcium gluconate, calcium lactate, potassium chloride, potassium sulfate, sodium chloride, potassium fluoride, ferrous lactate, ferrous gluconate, ferrous sulfate, ferrous fumurate and sodium lactate.

Representative drugs that act on α-adrenergic receptors are clonidine hydrochloride, prazosin, tamsulosin, terazosin, and doxazosin.

Representative mild CNS stimulants are caffeine, modafinil, and methylphenidate hydrochloride.

The active agents (drugs) listed herein should not be considered exhaustive and is merely exemplary of the many embodiments considered within the scope of the invention. Many other active agents can be administered with the formulation of the present invention. Suitable drugs are selected from the list of drugs included herein as well as from any other drugs accepted by the U.S.F.D.A. or other similarly recognized authority in Canada (Health Canada), Mexico (Mexico Department of Health), Europe (European Medicines Agency (EMEA)), South America (in particular in Argentina (Administración Nacional de Medicamentos, Alimentos y Tecnologiá Médica (ANMAT) and Brazil (Ministério da Sáude)), Australia (Department of Health and Ageing), Africa (in particular in South Africa (Department of Health) and Zimbabwe (Ministry of Health and Child Welfare),) or Asia (in particular Japan (Ministry of Health, Labour and Welfare), Taiwan (Executive Yuans Department of Health), and China (Ministry of Health People's Republic of China)) as being suitable for administration to humans or animals. Some embodiments of the invention include those wherein the active substance is pharmacologically or biologically active or wherein the environment of use is the GI tract of a mammal.

The amount of therapeutic compound incorporated in each dosage form will be at least one or more unit doses and can be selected according to known principles of pharmacy. An effective amount of therapeutic compound is specifically contemplated. By the term "effective amount", it is understood that, with respect to, for example, pharmaceuticals, a pharmaceutically effective amount is contemplated. A pharmaceutically effective amount is the amount or quantity of a drug or pharmaceutically active substance which is sufficient to elicit the required or desired therapeutic response, or in other words, the amount which is sufficient to elicit an appreciable biological response when administered to a patient. The appreciable biological response may occur as a result of administration of single or multiple unit doses of an active substance. A unit dose of the laminate can comprise about 0.1-30 mg of testosterone.

The term "unit dose" is used herein to mean a dosage form containing a quantity of the therapeutic compound, said quantity being such that one or more predetermined units may be provided as a single therapeutic administration.

The physical dimensions of a unit dose of the laminate will vary according to the physical dimensions of the individual reservoir and backing layers as well as according to the concentration and amount of testosterone present in the reservoir layer. In general, and in particular for transmucosal administration, the laminate may be shaped as square, rectangle or oval, and the surface area of the contact surface of the reservoir layer in a unit dose will be within the range of about 0.1-3 cm$^2$. The thickness (height) of the laminate will be less than or equal to about 2.0 mm.

The total amount of testosterone in a unit dose can be within the range of about 0.1-20 mg or 0.1-30 mg. Therefore, the concentration of testosterone in the reservoir layer would be within the range of about 6-33 mm$^2$/mg.

A dosage form according to the invention that comprises two or more active agents can include subtherapeutic amounts of one or more of those active agents such that an improved, additive or synergistic clinical benefit is provided by the dosage form. By "subtherapeutic amount" is meant an amount less than that typically recognized as being therapeutic on its own in a subject to which the dosage form is administered. Therefore, a dosage form can comprise a subtherapeutic amount of a first drug and a therapeutic amount of a second drug. Alternatively, a dosage form can comprise a subtherapeutic amount of a first drug and a subtherapeutic amount of a second drug.

The laminate is administered transdermally by placing a unit dose size of the laminate in contact with a dermal surface, such as the skin or a mucosal surface. There should be sufficient amount of moisture on the dermal surface to wet the contact surface of the laminate thereby initiating bioadhesion of the laminate onto the dermal surface. When administered buccally, the laminate can be administered such that the bioadhesive contact surface is in direct contact with the mucosa anywhere within the buccal cavity. For example, the mucosa can be from the gum, inner cheek, inner lip, or sublingual mucosal surfaces. The optionally-inert backing layer (meaning it might or might not be inert) may be non-bioadhesive thus eliminating undesirable adhesion to opposing mucosal surfaces. For example, a laminate placed on the distal surface of the gum will not simultaneously also adhere to the inner cheek or inner labial surfaces. The backing layer may be substantially impermeable to diffusion of testosterone, meaning that less than 10% or less than 5% of the charge of testosterone in the reservoir layer is released through the backing layer.

In view of the above description and the examples below, one of ordinary skill in the art will be able to practice the invention as claimed without undue experimentation. The foregoing will be better understood with reference to the following examples that detail certain procedures for the preparation of formulations according to the present invention. All references made to these examples are for the purposes of illustration. The following examples should not be considered exhaustive, but merely illustrative of only a few of the many embodiments contemplated by the present invention.

EXAMPLE 1

Preparation of a Bi-Layered Laminate by Hot-Melt Extrusion of Both Layers

The ingredients of the drug reservoir layer are hot-melt extruded as described herein. The ingredients of the backing layer are hot-melt extruded in a manner substantially similar to the procedure used for the reservoir layer. The two layers are then laminated to one another by heat-catalyzed lamination in which the two layers are pressed together while heated.

The ingredients for the hot-melt extruded drug reservoir layer are as follows:

| Raw Material | % w/w |
|---|---|
| Active agent | 1-30 |
| Alkaline Thermoplastic Bioadhesive Polymer | 10-99 |
| Optional Antioxidant | 0-10 |
| Optional Acidic Component | 0-40 |
| Optional Hydrophilic polymer | 0-75 |
| Optional Hydrophobic polymer | 0-75 |
| Optional water soluble and/or erodible polymer | 0-50 |
| Optional bioadhesive polymer | 0-50 |
| Optional Thermoplastic Polymer | 0-60 |
| Optional Plasticizer | 0-20 |
| Optional thermal lubricant | 0-20 |
| Optional Opaquant | 0-5 |

The hot-melt extruded backing layer comprises at least one thermoplastic polymer and at least one hydrophobic polymer. One or more other thermoplastic polymers are optionally included in the backing layer. One or more plasticizers are optionally included in the backing layer. One or more other hydrophobic polymers are optionally included in the backing layer. One or more hydrophilic polymers are optionally included in the backing layer. One or more opaquants are included in the backing layer. One or more thermal lubricants are optionally included in the backing layer. One or more antioxidants are optionally included in the backing layer. One or more other excipients are optionally included in the backing layer. Suitable ranges for the amounts of each ingredient are detailed below.

| Raw Material | % w/w |
|---|---|
| Thermoplastic Polymer | 30-90 |
| Hydrophobic polymer | 25-85 |
| Optional Hydrophilic polymer | 0-50 |
| Optional Thermoplastic Polymer | 0-50 |
| Optional Acidic Component | 0-40 |
| Optional Plasticizer | 0-20 |
| Optional Antioxidant | 0-10 |
| Optional thermal lubricant | 0-20 |
| Optional Opaquant | 0-5 |

EXAMPLE 2

The following process was used to prepare a hot-melt extruded composition according to the invention. The following ingredients in the amounts indicated were used in preparing hot-melt extruded control and sample compositions containing testosterone (Ts) as the active agent.

Method A. Hot-Melt Extrusion of Reservoir Layer

A Randcastle Taskmaster hot-melt extruder equipped with a 6-inch flat (sheet or film) die was operated at 60-90 RPM, 6-9 Drive Amps with an Extrusion Temperature from about 65-135° C. to prepare the composition. All powders were blended in a v-shell blender prior to extrusion. Temperature zones were set as follows: zone 1: 65° C., zone 2: 120° C., zone 3: 125° C., zone 4: 135° C., die temperature 135° C. The powder blend was placed in a feed hopper that is located at the head of a horizontal screw such that the material is starve fed by a mass flow controller operated at 1.5 kg/hr. The residence time of the material in the extruder was approximately three to five minutes. The extrudate was cut into approximately one-foot sections after exiting the die and placed on an aluminum sheets and allowed to cool at ambient conditions. In one embodiment, the granulated wet mass was placed in the feed hopper.

Alternate processing temperature schemes include:

| Zone | Temperature (° C.) |
|---|---|
| 1 | 65 |
| 2 | 85 |
| 3 | 95 |
| 4 | 105 |
| Die | 105 |
| 1 | 65 |
| 2 | 120 |
| 3 | 125 |
| 4 | 135 |
| Die | 135 |
| 1 | 65 |
| 2 | 125 |
| 3 | 135 |
| 4 | 140 |
| Die | 135 |

Method B. Hot-Melt Extrusion of Backing Layer.

A Randcastle Taskmaster hot-melt extruder equipped with a 6-inch flat die (a sheet-type dual manifold extrusion assembly) was operated at 60-90 RPM, 6-9 Drive Amps with an Extrusion Temperatures from 65-135° C. to prepare the composition. All powders were blended in a v-shell blender prior to extrusion. Temperature zones were set as follows: zone 1: 65° C., zone 2: 120° C., zone 3: 130° C., zone 4: 130° C., adapter: 135° C., transfer tube: 135° C., die temperature 140° C. The powder blend was placed in a hopper that is located at the head of a horizontal screw such that the material is starve fed by a mass flow controller operated at 0.5 kg/hr. The residence time of the material in the extruder was approximately five minutes. The extrudate was cut into approximately one-foot sections after exiting the die and placed on an aluminum sheets and allowed to cool at ambient conditions.

EXAMPLE 3

Exemplary formulations for use as the reservoir composition used to form the laminate.

The following ingredients in the amounts indicated were used in preparing hot-melt extruded sample compositions containing testosterone (Ts) as the active agent.

Formulation I

| Raw Material | % w/w |
|---|---|
| Testosterone, USP | 15.00 |
| PolyOx WSR N80 | 26.85 |
| PolyOx WSR N12K | 20.36 |
| PolyOx WSR 301 | 16.79 |
| Carbopol 974P | 10.00 |
| Vitamin E Succinate | 5.00 |
| Titanium Dioxide | 1.00 |
| Poloxamer 407 | 5.00 |

Formulation ii

| Raw Material | % w/w |
|---|---|
| Testosterone, USP | 15.00 |
| PolyOx WSR N80 | 26.85 |
| PolyOx WSR N12K | 20.36 |
| PolyOx WSR 301 | 16.79 |
| Carbopol 974P | 10.00 |
| Citric Acid Monohydrate | 1.00 |
| Butylated Hydroxytoluene | 4.00 |
| Titanium Dioxide | 1.00 |
| Poloxamer 407 | 5.00 |

Formulation iii

| Raw Material | % w/w |
|---|---|
| Testosterone, USP | 15.00 |
| PolyOx WSR N80 | 26.85 |
| PolyOx WSR N12K | 20.36 |
| PolyOx WSR 301 | 16.79 |
| Carbopol 974P | 10.00 |
| Citric Acid Monohydrate | 5.00 |
| Titanium Dioxide | 1.00 |
| Poloxamer 407 | 5.00 |

Formulation iv

| Raw Material | % w/w |
|---|---|
| Testosterone, USP | 15.00 |
| PolyOx WSR N80 | 26.85 |
| PolyOx WSR N12K | 20.36 |
| PolyOx WSR 301 | 16.79 |
| Carbopol 974P | 10.00 |
| Butylated Hydroxytoluene | 4.00 |
| Titanium Dioxide | 1.00 |
| Poloxamer 407 | 6.00 |

Formulation v

| Raw Material | % w/w |
|---|---|
| Testosterone, USP | 15.00 |
| PolyOx WSR N80 | 26.85 |
| PolyOx WSR N12K | 18.86 |
| PolyOx WSR 301 | 16.79 |
| Carbopol 974P | 10.00 |
| Butylated Hydroxytoluene | 4.00 |
| Titanium Dioxide | 1.00 |
| Poloxamer 407 | 7.50 |

Formulation vi

| Raw Material | % w/w |
|---|---|
| Testosterone, USP | 15.00 |
| PolyOx WSR N80 | 26.85 |
| PolyOx WSR N12K | 19.36 |
| PolyOx WSR 301 | 16.79 |
| Carbopol 974P | 10.00 |
| Butylated Hydroxytoluene | 2.00 |
| Titanium Dioxide | 1.00 |
| Poloxamer 407 | 9.00 |

Formulation SR4

| Raw Material | % w/w |
|---|---|
| PolyOx WSR N80 | 72.00 |
| Testosterone, USP | 20.00 |
| Polycarbophil | 2.00 |
| Vitamin E Succinate | 5.00 |
| Titanium Dioxide | 1.00 |

Formulation SR12

| Raw Material | % w/w |
|---|---|
| PolyOx WSR N80 | 43.20 |
| PolyOx WSR N12K | 28.80 |
| Testosterone, USP | 20.00 |
| Polycarbophil | 2.00 |
| Vitamin E Succinate | 5.00 |
| Titanium Dioxide | 1.00 |

Formulations A-D

| Component | Formulation (% w/w) | | | |
|---|---|---|---|---|
| | A | B | C | D |
| PolyOx WSR N80 | 43.20 | 45.50 | 43.00 | 34.00 |
| PolyOx WSR N12K | 30.80 | 32.50 | 21.00 | 27.00 |
| PolyOx WSR 301 | | | 10.00 | 18.00 |
| Testosterone, USP | 20.00 | 16.00 | 20.00 | 15.00 |
| Vitamin E Succinate | 5.00 | 5.00 | 5.00 | 5.00 |
| Titanium Dioxide | 1.00 | 1.00 | 1.00 | 1.00 |
| Testosterone Dose (mg) | 20 | 20 | 20 | 15 |

Formulations E-J

| Component | Formulation (% w/w) | | | | | |
|---|---|---|---|---|---|---|
| | E | F | G | H | I | J |
| PolyOx WSR N80 | 36.01 | 34.00 | 38.16 | 33.86 | 33.86 | 36.01 |
| PolyOx WSR N12K | 28.64 | 27.00 | 30.35 | 14.96 | 14.96 | 15.91 |
| PolyOx WSR 301 | 19.10 | 18.00 | 20.24 | 29.93 | 29.93 | 31.83 |
| Testosterone, USP | 10.00 | 10.00 | 5.00 | 15.00 | 15.00 | 10.00 |
| Vitamin E Succinate | 5.00 | 5.00 | 5.00 | 5.00 | 5.00 | 5.00 |
| Carbopol 974P | 0.25 | 5.00 | 0.25 | 0.25 | 0.25 | 0.25 |
| Titanium Dioxide | 1.00 | 1.00 | 1.00 | 1.00 | 1.00 | 1.00 |
| Testosterone Dose (mg) | 10.0 | 10.0 | 5.0 | 15.0 | 12.5 | 10.0 |

Formulation K

| Component | % w/w |
|---|---|
| PolyOx WSR N80 | 32.90 |
| PolyOx WSR N12K | 26.16 |
| PolyOx WSR 301 | 17.44 |
| Carbopol 974P | 5.00 |
| Testosterone, USP | 12.50 |
| Vitamin E Succinate | 5.00 |
| Titanium Dioxide | 1.00 |
| Testosterone Dose (mg) | 12.5 |

EXAMPLE 4

Determination of Drug Release

Samples from the beginning, middle and end of a lot of extruded laminate (reservoir layer containing testosterone and backing layer excluding drug) were sampled and dissolution studies were conducted in 1,000 mL of Simulated Saliva Fluid (0.1% sodium lauryl sulfate at pH 6.75) at 100 rpm using the paddles. Samples were withdrawal at 1, 2, 4, 6, 8, 12 and 24 hours and assayed for testosterone content by HPLC. The HPLC method employed will vary according to the drug included in the HME composition. Such methods are found in *HPLC in the Pharmaceutical Industry* (edited by Godwin W. Fong, Stanley K. Lam, New York: M. Dekker, 1991) or *HPLC Methods for Pharmaceutical Analysis* (by George Lunn and Norman R. Schmuff. New York: John Wiley & Sons, 1997).

The doses were tested in vitro using simulated saliva fluid (0.10% sodium lauryl sulfate adjusted to pH 6.75±0.05 with phosphoric acid) at 37.0±0.5° C. using the Paddle Method (100 rpm) with Ointment Disks covered with a 17 mesh Teflon screen. The paddle height was adjusted 2.5 cm above the top of the ointment disks. Samples (3 mL) were withdrawn and the media replaced from each vessel at 1, 2, 4, 6, 8 and 12 hours and filtered through a 10 μm polyethylene free-flow dissolution filter into a labeled test tube. The resultant samples were analyzed for testosterone content by a gradient HPLC method using a Prodigy™ ODS-2, 5 μm, 150 Å, 4.6× 250 mm column at 243 nm wavelength of detection. Mobile phase A was 55/45 Methanol/Water, v/v and Mobile Phase B was 100% Methanol. The flow rate was 1.0 mL/min, the column temperature was 40° C., the injection volume was 25 μL and the run time was 25 minutes.

EXAMPLE 5

Preparation of a Backing Film

Method A.

An exemplary backing film was prepared by hot-melt extrusion of a hydrophobic composition containing the following ingredients in the specified amounts.

| Raw Material | % w/w |
| --- | --- |
| PolyOx WSR N80 | 10.00 |
| PolyOx WSR 205 | 7.50 |
| PolyOx WSR 301 | 36.50 |
| Eudragit RS PO | 35.00 |
| Ethyl Cellulose Std 100 | 6.25 |
| FD&C Red 40 Lake | 0.15 |
| Titanium Dioxide | 0.60 |
| Citric Acid, monohydrate | 1.00 |
| Dibutyl Sebacate | 3.00 |

Method B:

Another exemplary backing film was prepared by hot-melt extrusion of a hydrophobic composition containing the following ingredients in the specified amounts.

| Raw Material | % w/w |
| --- | --- |
| PolyOx WSR N80 | 5.00 |
| PolyOx WSR 205 | 5.00 |
| PolyOx WSR 301 | 45.00 |
| Eudragit RS PO | 35.00 |
| Ethyl Cellulose Std 100 | 6.25 |
| FD&C Red 40 Lake | 0.15 |
| Titanium Dioxide | 0.60 |
| Citric Acid, monohydrate | 1.00 |
| Dibutyl Sebacate | 3.00 |

EXAMPLE 6

Preparation of a Bi-Layered Laminate by Coextrusion

An exemplary bi-layered laminate comprising a backing layer and a reservoir layer was prepared by hot-melt coextrusion of a hydrophobic composition (as described in Example 5) and a hydrophilic composition, respectively, containing the following ingredients in the specified amounts.

| Reservoir Layer (Hydrophilic composition) | | |
| --- | --- | --- |
| | % w/w | |
| Compound | Lot 1 | Lot 2 |
| Testosterone, USP | 15.00 | 15.00 |
| PolyOx WSR N80 | 26.85 | 26.85 |
| PolyOx WSR N12K | 18.36 | 18.36 |
| PolyOx WSR 301 | 16.29 | 13.79 |
| Carbopol 974P | 12.50 | 15.00 |
| Vitamin E Succinate | 3.00 | 3.00 |
| Vitamin E | 2.00 | 2.00 |
| Titanium Dioxide | 1.00 | 1.00 |
| Poloxamer F127 | 5.00 | 5.00 |
| Total | 100.00 | 100.00 |

The films were extruded with the acidified backing film formulation as described above. The drug layer thickness was 1.10 mm and the backing film thickness was 0.40 mm. Doses were cut to provide a 15 mg Testosterone dose.

EXAMPLE 7

Preparation of a Bi-Layered Laminate by Coextrusion

A clinical formulation was modified to achieve a slower dissolution profile. The testosterone concentration was lowered from 15% to 8.18% and the carbopol concentration was increased from 10% to 15%. The batch was prepared using Disoynth sourced testosterone by wet granulation acidification with 5%, 50 mM hydrochloric acid and 5% ethanol. The granulation was coextruded with the acidified backing film. These blends were coextruded as a bi-layered laminate at a 2.75:1 drug layer to backing layer ratio and overall target thickness of 1.50 mm using the Randcastle coextrusion line at 135° C. maximum processing temperature. The moisture content of the blend prior to extrusion was 2.0%.

EXAMPLE 8

Preparation of a Bi-Layered Laminate by Coextrusion

The methods of Example 2 were followed to prepare a bi-layered laminate comprising the following ingredients in the specified amounts.

| Reservoir layer | |
| --- | --- |
| Raw Material | % w/w |
| Testosterone, USP | 8.18 |
| PolyOx WSR N80 | 26.85 |
| PolyOx WSR N12K | 22.18 |
| PolyOx WSR 301 | 16.79 |
| Carbopol 974P | 15.00 |
| Vitamin E Succinate | 5.00 |
| Titanium Dioxide | 1.00 |
| Poloxamer 407 | 5.00 |

| Backing layer | |
| --- | --- |
| Raw Material | % w/w |
| PolyOx WSR N80 | 10.00 |
| PolyOx WSR 205 | 7.50 |
| PolyOx WSR 301 | 36.50 |
| Eudragit RS PO | 35.00 |
| Ethyl Cellulose Std 100 | 6.25 |
| FD&C Red 40 Lake | 0.15 |
| Titanium Dioxide | 0.60 |
| Citric Acid, monohydrate | 1.00 |
| Dibutyl Sebacate | 3.00 |

EXAMPLE 9

Preparation of a Bi-Layered Laminate by Coextrusion

The methods of Example 2 were followed to prepare a bi-layered laminate comprising the following ingredients in the specified amounts. The formulation of the backing layer was as described in Example 5.

| Reservoir layer | |
|---|---|
| Raw Material | % w/w |
| Testosterone, USP | 8.18 |
| PolyOx WSR N80 | 23.67 |
| PolyOx WSR N12K | 20.36 |
| PolyOx WSR 301 | 16.79 |
| Carbopol 974P | 15.00 |
| Glyceryl Monooleate | 5.00 |
| Vitamin E Succinate | 5.00 |
| Titanium Dioxide | 1.00 |
| Poloxamer 407 | 5.00 |

The melt viscosity of the formulation was significantly increased as compared to another formulation containing less Carbopol. Processing conditions were modified to avoid over pressurizing the extruder. The screw speed was increased by 22% and the feed rate was decreased by 46% to achieve acceptable pressure at the adapter.

EXAMPLE 9

Preparation of Multiple Unit Doses from a Hot-Melt Coextruded Bi-Layered Laminate The laminate was cut into manageable sub-lengths after coextrusion. Each sub-length was then cut (divided) into unit dose portions. Alternatively, the laminate was cut directly into unit doses following lamination. In some embodiments, the active agent in the unit dose is testosterone. Exemplary unit doses were made as follows:

Method A: 20 mg strength testosterone unit dose

| Formulation | SR4 | SR12 | A | B | C | D |
|---|---|---|---|---|---|---|
| Unit Dose Strength (mg) | 20 | 20 | 20 | 20 | 20 | 20 |
| Unit Dose Avg. Weight (mg) | 109.5 | 107.9 | 186 | 214 | 171 | 173 |
| Unit Dose Avg. Length (mm) | 20.77 | 11.74 | 15.15 | 16.62 | 14.98 | 15.67 |
| Unit Dose Avg. Width (mm) | 11.61 | 9.7 | 9.65 | 10.16 | 9.78 | 9.8 |
| Unit Dose Avg. Thickness (mm) | 0.42 | 0.87 | 1.23 | 1.27 | 1.22 | 1.13 |
| Unit Dose Avg. Surface Area ($mm^2$) | 241 | 114 | 146 | 169 | 146 | 154 |
| Unit Dose Avg. Surface Area to dose ratio ($mm^2/mg$) | 12.1 | 5.7 | 7.3 | 8.45 | 7.3 | 10.3 |

Method B: Other testosterone unit doses

| | Formulation | | | | | | |
|---|---|---|---|---|---|---|---|
| | E | F | G | H | I | J | K |
| Unit Dose Strength (mg) | 10 | 10 | 5 | 15 | 12.5 | 10 | 12.5 |
| Unit Dose Avg. Weight (mg) | 156 | 157 | 164 | 168 | 151 | 158 | 155 |
| Unit Dose Avg. Length (mm) | 22.42 | 21.51 | 21.47 | 21.9 | 19.29 | 22.41 | 21.03 |
| Unit Dose Avg. Width (mm) | 6.46 | 6.31 | 6.36 | 6.48 | 6.29 | 6.48 | 6.29 |
| Unit Dose Avg. Thickness (mm) | 1.12 | 1.16 | 1.21 | 1.2 | 1.2 | 1.13 | 1.17 |
| Unit Dose Avg. Surface Area ($mm^2$) | 145 | 133 | 137 | 142 | 121 | 145 | 132 |
| Unit Dose Avg. Surface Area to dose ratio ($mm^2/mg$) | 14.5 | 13.3 | 32.8 | 9.5 | 9.7 | 14.5 | 10.6 |

EXAMPLE 10

Preparation of a Bi-Layered Laminate by Hot-Melt Coextrusion

The powdered ingredients in following tables were blended to form their respective compositions and then hot-melt coextruded into a bilayered laminate according to the conditions detailed below.

| Reservoir layer formulations | | | | |
|---|---|---|---|---|
| | L | M | N | P |
| Testosterone, USP | 12.50 | 12.50 | 15.00 | 15.00 |
| PolyOx WSR N80 | 27.90 | 27.90 | 26.85 | 26.85 |
| PolyOx WSR N12K | 21.16 | 21.16 | 20.36 | 20.36 |
| PolyOx WSR 301 | 17.44 | 17.44 | 16.79 | 16.79 |
| Carbopol 974P | 10.00 | 10.00 | 10.00 | 10.00 |
| Vitamin E Succinate | 5.00 | 5.00 | 5.00 | 5.00 |
| Titanium Dioxide | 1.00 | 1.00 | 1.00 | 1.00 |
| Poloxamer 407 | 5.00 | 5.00 | 5.00 | 5.00 |
| Testosterone Dose (mg) | 12.5 | 12.5 | 15 | 15 |

| Hot-melt Processing Parameters | | | |
|---|---|---|---|
| Extruder A: (Drug Film) | | Extruder B: (Backing Film) | |
| Heating Zone | Temperature (° C.) | Heating Zone | Temperature (° C.) |
| Zone 1 | 65 | Zone 1 | 65 |
| Zone 2 | 120 | Zone 2 | 120 |
| Zone 3 | 140 | Zone 3 | 130 |
| Zone 4 | 145 | Zone 4 | 130 |
| Adapter | 145 | Adapter | 135 |
| Transfer Tube | 145 | Transfer Tube | 135 |
| Feed Block | 145 | Die | 140 |

| Poorly Permeable-Backing Layer Formulations | |
|---|---|
| PolyOx WSR N80 | 5.00 |
| PolyOx WSR 205 | 5.00 |
| PolyOx WSR 301 | 45.00 |
| Methacrylic Acid Copolymer | 35.00 |
| Ethyl Cellulose | 6.25 |
| FD&C Red 40 Lake | 0.15 |
| Titanium Dioxide | 0.60 |
| Dibutyl Sebacate | 3.00 |

Figure 12:
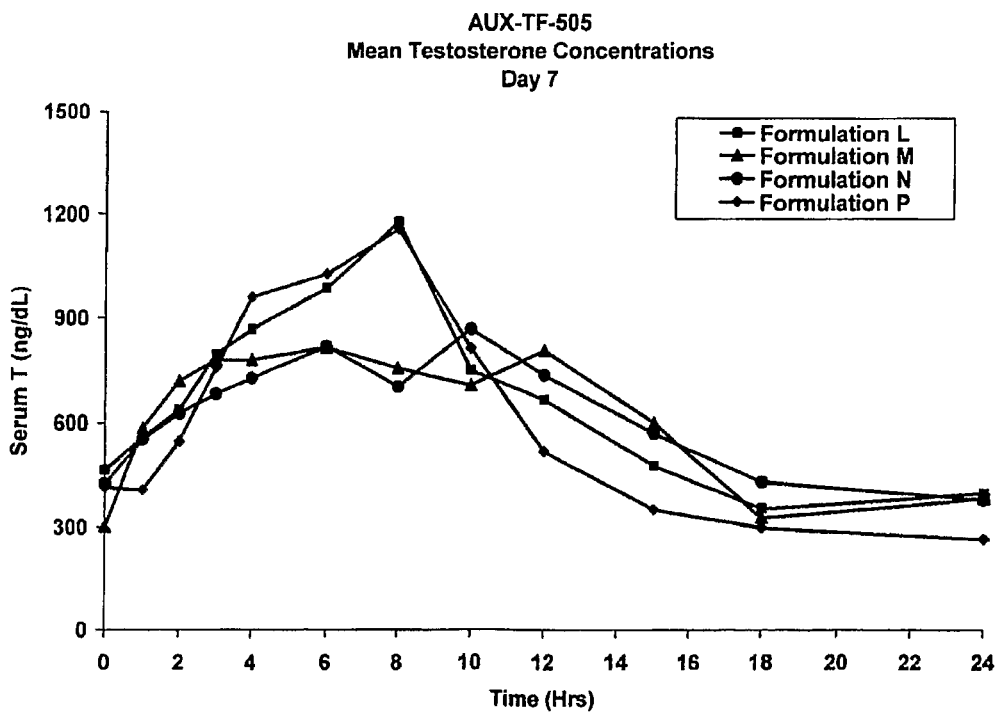
FIG. 12 depicts in vivo plasma profiles for Formulations L-P.

The resultant bi-layered laminates were cut into unit doses exhibiting unidirectional drug release as depicted in the in vitro release profiles (FIG. 11) and in vivo release profiles (FIG. 12). The unit dose size and dose strengths obtained are detailed below.

| | SAMPLE | | | |
|---|---|---|---|---|
| | L | M | N | P |
| Unit Dose Strength (mg) | 12.5 | 12.5 | 15 | 15 |
| Unit Dose Avg. Weight (mg) | 155 | 135 | 130 | 145 |
| Unit Dose Avg. Length (mm) | 18.17 | 15.76 | 14.58 | 15.1 |
| Unit Dose Avg. Width (mm) | 6.29 | 6.28 | 6.28 | 6.28 |
| Unit Dose Avg. Thickness (mm) | 1.21 | 1.19 | 1.22 | 1.35 |
| Unit Dose Avg. Surface Area (mm$^2$) | 114 | 99 | 91.5 | 95 |
| Unit Dose Avg. Surface Area to dose ratio (mm$^2$/mg) | 9.1 | 7.9 | 6.1 | 6.3 |

EXAMPLE 11

Exemplary Formulations for an Acid-Stabilized Composition in a Reservoir Layer of the Laminate of Invention Method A.

| Raw Material | % w/w |
|---|---|
| Testosterone | 5-20 |
| Thermoplastic Bioadhesive Polymer | 40-85 |
| Acidic Component | 0.001-10 |
| Optional Antioxidant | 0-10 |
| Optional Hydrophilic polymer | 0-75 |
| Optional Hydrophobic polymer | 0-75 |
| Optional Bioadhesive polymer | 0-50 |
| Optional Thermoplastic Polymer | 0-60 |
| Optional Plasticizer | 0-20 |
| Optional thermal lubricant | 0-10 |
| Optional Opaquant | 0-5 |

Method B.

| Raw Material | % w/w |
|---|---|
| Testosterone | 5-20 |
| PEO | 5.00-75.0 |
| Acidic Component | 0.01-15.00 |
| Antioxidant | 0.10-25.00 |
| Optional Hydrophilic polymer | 0.00-50.00 |
| Optional Hydrophobic polymer | 0.00-60.00 |
| Optional bioadhesive polymer | 0.001-10.00 |
| Optional Thermoplastic Polymer | 0.00-25.00 |
| Optional Plasticizer | 0.00-10.00 |
| Optional thermal lubricant | 0.00-20.00 |
| Optional Opaquant | 0.00-5.00 |

Method C.

| Raw Material | % w/w |
|---|---|
| Testosterone | 5-20 |
| PEO | 5.00-75.0 |
| Polymeric Acidic Component | 0.25-35.00 |
| Optional Non-polymeric acidic component | 0.00-15.00 |
| Antioxidant | 0.10-25.00 |
| Hydrophilic polymer | 2.00-10.00 |
| Optional Hydrophobic polymer | 0.00-50.00 |
| Optional bioadhesive polymer | 0.00-60.00 |
| Optional Thermoplastic Polymer | 0.00-20.00 |
| Optional Plasticizer | 0.00-10.00 |
| Optional Opaquant | 0.00-20.00 |
| | 0.00-5.00 |

Method D.

| Raw Material | % w/w |
|---|---|
| Testosterone | 5-20 |
| PEO Grade 1 | 5.00-50.00 |
| PEO Grade 2 | 5.00-50.00 |
| PEO Grade 3 | 5.00-50.00 |
| Polymeric Acidic Component | 0.25-35.00 |
| Antioxidant | 0.10-25.00 |
| Hydrophilic polymer | 5.00-10.00 |
| Optional Non-polymeric Acidic Component | 0.00-75.00 |

-continued

| Raw Material | % w/w |
|---|---|
| Optional Hydrophobic polymer | 0.00-50.00 |
| Optional bioadhesive polymer | 0.00-60.00 |
| Optional Thermoplastic Polymer | 0.00-20.00 |
| Optional Thermal Lubricant | 0.00-20.00 |
| Optional Plasticizer | 0.00-10.00 |
| Optional Opaquant | 0.00-5.00 |

Method E.

| Raw Material | % w/w |
|---|---|
| Testosterone | 5-20 |
| PEO Grade 1 | 5.00-50.00 |
| PEO Grade 2 | 5.00-50.00 |
| PEO Grade 3 | 5.00-50.00 |
| CARBOPOL | 0.25-25.00 |
| POLOXAMER | 2.00-10.00 |
| Antioxidant | 0.10-20.00 |
| Opaquant | 0.25-5.00 |
| Optional Non-polymeric Acidic Component | 0.00-50.00 |
| Optional Hydrophobic polymer | 0.00-60.00 |
| Optional Bioadhesive Polymer | 0.00-20.00 |
| Optional Thermoplastic Polymer | 0.00-20.00 |
| Optional Thermal Lubricant | 0.00-10.00 |
| Optional Plasticizer | 0.00-15.00 |

Figure 13A:
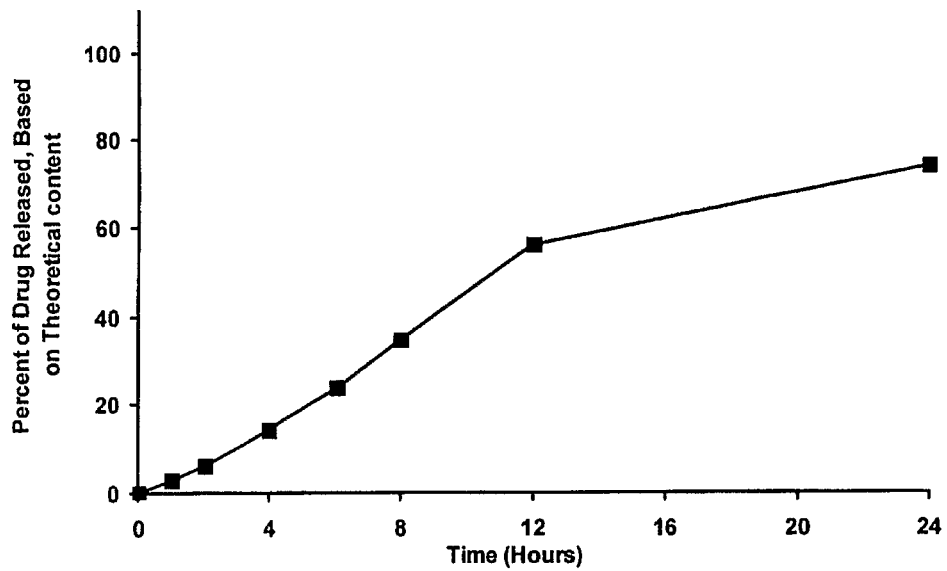
FIGS. 13a and 13b depict release profiles for various different extended release HME compositions made according to Example 11.
Figure 13B:
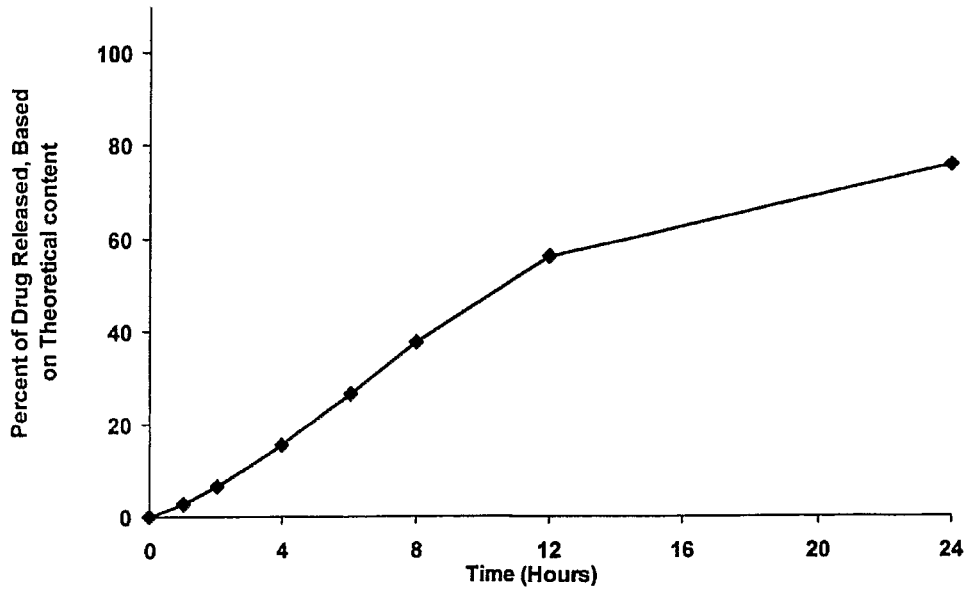

In vitro release profiles for some exemplary laminates made according to this example are depicted in FIGS. 13a and 13b.

EXAMPLE 12

Exemplary formulations for a hot-melt extruded backing layer in a laminate of the invention.

Method A.

| Raw Material | % w/w |
|---|---|
| Thermoplastic Polymer | 10.00-99.90 |
| Hydrophobic polymer | 5.00-10.00 |
| Optional Hydrophilic polymer | 0.00-50.00 |
| Optional Thermoplastic Polymer | 0.00-75.00 |
| Optional Acidic Component | 0.00-10.00 |
| Optional Plasticizer | 0.00-20.00 |
| Optional Antioxidant | 0.00-15.00 |
| Optional thermal lubricant | 0.00-20.00 |
| Optional Opaquant | 0.00-5.00 |

Method B.

| Raw Material | % w/w |
|---|---|
| PEO | 5.00-75.00 |
| Hydrophobic polymer | 5.00-55.00 |
| Optional Hydrophilic polymer | 0.00-50.00 |
| Optional Thermoplastic Polymer | 0.00-75.00 |
| Optional Acidic Component | 0.00-10.00 |
| Optional Plasticizer | 0.00-20.00 |
| Optional Antioxidant | 0.00-15.00 |
| Optional thermal lubricant | 0.00-20.00 |
| Optional Opaquant | 0.00-5.00 |

Method C.

| Raw Material | % w/w |
|---|---|
| PEO Grade 1 | 5.00-50.00 |
| PEO Grade 2 | 5.00-50.00 |
| PEO Grade 3 | 5.00-50.00 |
| Hydrophobic polymer | 5.00-55.00 |
| Optional Hydrophilic polymer | 0.00-50.00 |
| Optional Thermoplastic Polymer | 0.00-75.00 |
| Optional Acidic Component | 0.00-10.00 |
| Optional Plasticizer | 0.00-20.00 |
| Optional Antioxidant | 0.00-15.00 |
| Optional thermal lubricant | 0.00-20.00 |
| Optional Opaquant | 0.00-5.00 |

Method D.

| Raw Material | % w/w |
|---|---|
| PEO Grade 1 | 5.00-50.00 |
| PEO Grade 2 | 5.00-50.00 |
| PEO Grade 3 | 5.00-50.00 |
| Polyacrylate polymer | 10.00-85.00 |
| Ethyl Cellulose | 1.00-45.00 |
| Optional Thermoplastic Polymer | 0.00-75.00 |
| Optional Acidic Component | 0.00-10.00 |
| Optional Plasticizer | 0.00-20.00 |
| Optional Antioxidant | 0.00-15.00 |
| Optional thermal lubricant | 0.00-20.00 |
| Optional Opaquant | 0.00-5.00 |

EXAMPLE 13

ASTM method D1238 was used to determine the melt flow index of the active agent (hydrophilic) composition and the backing (hydrophobic) composition.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

What is claimed is:

1. A bioadhesive bi-layered hot-melt extruded laminate comprising a hydrophilic bioadhesive reservoir layer and a hydrophobic backing layer, wherein
   a) the bioadhesive reservoir layer comprises an active agent;
   b) each of the bioadhesive reservoir layer and the backing layer comprises poly(ethylene) oxide (PEO); and
   c) the backing layer comprises a hydrophilic polymer in a sufficiently low amount such that the backing layer is hydrophobic,
   wherein the PEO in each layer is selected from the group consisting of PEO Grade 1, PEO Grade 2, PEO Grade 3, and a combination thereof, wherein: PEO Grade 1 is polyethylene oxide with (i) a solution viscosity in the range of 12-8800 mPa·s at 25° C. in a 5% solution, or (ii) an approximate molecular weight range from 100,000-600,000; PEO Grade 2 is polyethylene oxide with (i) a solution viscosity in the range of 8800 mPa·S at 25° C. in a 5% solution to 4000 mPa·s at 25° C. in a 2% solution, or (ii) an approximate molecular weight range from 900,000-2,000,000; and PEO Grade 3 is polyethylene oxide with (i) a solution viscosity in the range of 1650-15,000 mPa-s at 25° C. in a 1% solution, or (ii) an approximate molecular weight range from 4,000,000-8,000,000, wherein the PEO in the bioadhesive reservoir layer comprises PEO Grade 1, PEO Grade 2, and PEO Grade 3.

2. The laminate of claim 1, wherein the backing layer comprises two or more hydrophobic polymers.

3. The laminate of claim 1, wherein the melt flow index of the reservoir layer is within 50% of the melt flow index of the backing layer.

4. The laminate of claim 1, wherein the laminate comprises a controlled, sustained, slow, extended, or targeted release therapeutic composition.

5. The laminate of claim 1, wherein the laminate comprises a dosage form adapted for transdermal, transmucosal, rectal, pulmonary, nasal, vaginal, ocular, or otic drug delivery, or as an implantable drug delivery device.

6. The laminate of claim 1, wherein the active agent is selected from the group consisting of testosterone, oxybutynin, morphine, fentanyl, aspirin, lansoprazole, omeprazole, pantoprazole, rabeprazole and naltrexone.

7. The laminate of claim 1, wherein each of the backing layer and the reservoir layer comprises at least 10% wt. of the PEO.

8. The laminate of claim 1 further comprising a release liner layer removably affixed to the reservoir layer.

9. The laminate of claim 1, wherein the reservoir layer comprises 40 to 90% by wt. of the laminate.

10. The laminate of claim 1, wherein the active agent is fentanyl.

11. The laminate of claim 1, wherein the active agent is testosterone.

12. The laminate of claim 1, wherein the bioadhesive reservoir layer further comprises an acidic component.

13. The laminate of claim 1, wherein the PEO in the backing layer comprises two or more grades of PEO selected from the group consisting of PEO Grade 1, PEO Grade 2, and PEO Grade 3.

14. The laminate of claim 1, wherein the reservoir layer comprises about 10% to about 70% wt. of the PEO.

15. A unit dose comprising a portion of a laminate according to claim 1, wherein the reservoir layer has an average exposed surface area between 90 and 250 mm$^2$.

16. The unit dose of claim 15 comprising a surface area to dose ratio of 5 to 35 mm$^2$/mg active agent based upon the exposed surface of the reservoir layer.

* * * * *